United States Patent
Zhou et al.

(10) Patent No.: US 7,645,857 B2
(45) Date of Patent: Jan. 12, 2010

(54) METHODS OF INDENTIFYING MODULATORS OF THE FGF RECEPTOR

(75) Inventors: Ming-Ming Zhou, Greenwich, CT (US); Mitchell Goldfarb, River Edge, NJ (US)

(73) Assignee: Mount Sinai School of Medicine, New York, NY (US)

( * ) Notice: Subject to any disclaimer, the term of this patent is extended or adjusted under 35 U.S.C. 154(b) by 164 days.

(21) Appl. No.: 11/183,567

(22) Filed: Jul. 18, 2005

(65) Prior Publication Data

US 2006/0019296 A1    Jan. 26, 2006

Related U.S. Application Data

(63) Continuation of application No. 09/757,415, filed on Jan. 9, 2001, now Pat. No. 7,108,984.

(60) Provisional application No. 60/175,867, filed on Jan. 12, 2000.

(51) Int. Cl.
*C07K 9/00* (2006.01)
*C07K 4/12* (2006.01)
*C07K 14/435* (2006.01)

(52) U.S. Cl. .................. 530/324; 530/325; 530/326

(58) Field of Classification Search .................. None
See application file for complete search history.

(56) References Cited

U.S. PATENT DOCUMENTS 5,767,250 A * 6/1998 Spaete .................. 530/395

OTHER PUBLICATIONS

Blaikie et al., *J. Biol. Chem.*, 269:32031-32034 (1994).
Clore et al., *Meth. Enzymol.*, 239:249-363 (1994).
Dhalluin et al., *Nature* 399:491-496 (1999).
Eck et al., *Cell*, 85:695-705 (1996).
Forman-Kay et al., *Curr. Opin. Struct. Biol.*, 9:690-695 (1999).
Gustafson et al., *Mol. Cell. Biol.*, 15:2500-2508 (1995).
Kavanaugh et al., *Science*, 268:1177-1179 (1995).
Kavanaugh et al., *Science*, 266:1862-1865 (1994).
Kouhara et al., *Cell*, 89:693-702 (1997).
Lemmon et al., *Cell*, 85:621-624 (1996).
Li et al., *Proc. Natl. Acad. Sci. USA*, 94:7204-7209 (1997).
Li et al., *Nat. Struct. Biol.*, 5:1075-1083 (1998).
Meakin et al., *J. Biol. Chem.*, 274:9861-9870 (1999).
O'Neill et al., *Mol. Cell. Biol.*, 14:6433-6442 (1994).
Ong et al., *Mol. Cell. Biol.*, 20:979-989 (2000).
Pawson et al., *Science*, 278:2075-2080 (1997).
Sattler et al., *Prog. in Nuclear Magnetic Resonance Spec.*, 4:93-158 (1999).
Shuker et al., *Science*, 274:1531-1534 (1996).
Songyang et al., *J. Biol. Chem.*, 270:14863-14866 (1995).
Trub et al., *J. Biol. Chem.*, 270:18205-18208 (1995).
Xu et al., *J. Biol. Chem.*, 273:17987-17990 (1998).
Yamazaki et al., *J. Am. Chem. Soc.*, 116:11655-11666 (1994).
Zhang et al., *EMBO J.*, 16:6141-6150 (1997).
Zhou et al., *J. Biol. Chem.*, 271:31119-31123 (1995).
Zhou et al., *Nature*, 378:584-592 (1995).
Zhou et al., *Nature Struct. Biol.*, 3:388-393 (1996).
Zwahlen et al., *EMBO J*, 19:1505-1515 (2000).

* cited by examiner

*Primary Examiner*—James Martinell
(74) *Attorney, Agent, or Firm*—Klauber & Jackson, LLC

(57) ABSTRACT

The present invention provides fragments of SNT and FGFR which can form a binding complex that is amenable to structural determinations by NMR spectroscopy. The three-dimensional structural data is also included as part of the invention. In addition, the present invention provides methodology for related structure based rational drug design using the three-dimensional data. Nucleotide and amino acid sequences of the fragments are also provided.

2 Claims, 9 Drawing Sheets

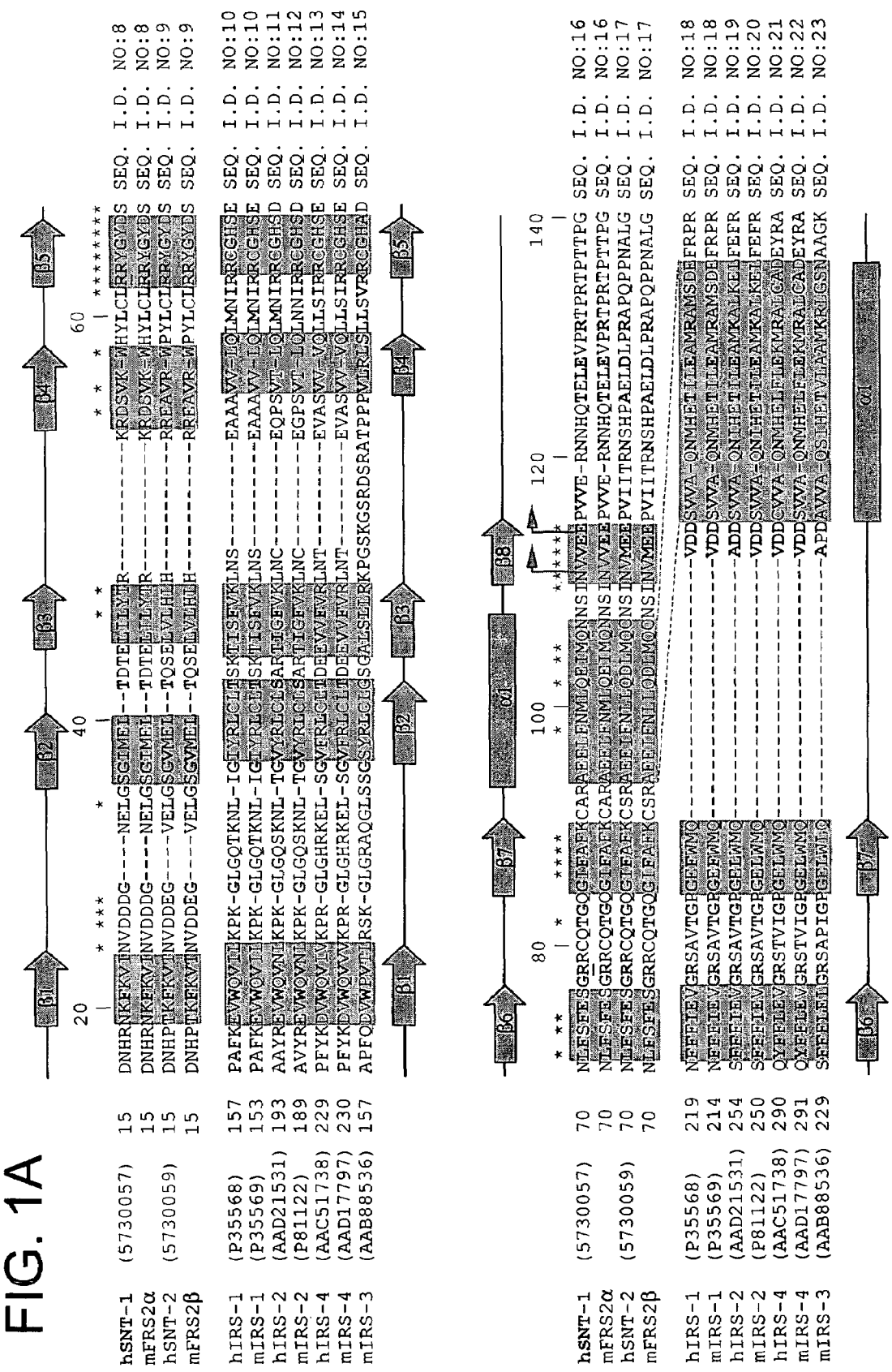

FIG. 1B

Intermolecular NOEs

```
                                      37 8 26 10 2 20    1 4 18   26 7 12 5 52 20 30 7
                                              415         420         425        430
```

| Name | Accession | Range | Sequence | SEQ ID |
|---|---|---|---|---|
| hFGFR1 | (P11362) | (409-430) | H S Q M A V H K I L A K H P L R Q V T V S | SEQ. I.D. NO:24 |
| mFGFR1 | (JH0393) | (419-440) | H S Q M A V H K I L A K H P L R Q V T V S | SEQ. I.D. NO:24 |
| xFGFR1 | (P22182) | (405-426) | N S Q L A V H K L A K H P V R Q V T V S | SEQ. I.D. NO:25 |
| hFGFR2 | (A45081) | (411-432) | S S Q P A V H K L T R R P P L R R Q V T V S | SEQ. I.D. NO:26 |
| mFGFR2 | (A38429) | (296-317) | S S Q P A V H K L T R R P P L R R Q V T V S | SEQ. I.D. NO:26 |
| xFGFR2 | (Q03364) | (400-421) | F T G P P V H K V S R P P V H R Q V S V S | SEQ. I.D. NO:27 |
| hFGFR3 | (NP_000133) | (407-426) | G S - I P T H H K L S - - F P L H R Q V S L E | SEQ. I.D. NO:28 |
| mFGFR3 | (Q61851) | (401-420) | G S - I P T H H K V S - - F P L K R Q V S L E | SEQ. I.D. NO:29 |
| xFGFR3 | (BAA22281) | (396-415) | T A - I P P V H K V S - - F P V K A Q V S L E | SEQ. I.D. NO:30 |
| hFGFR4 | (AAB59389) | (401-421) | R P P A T H V Q L R - - F P L A R Q V L L E | SEQ. I.D. NO:31 |
| mFGFR4 | (S18209) | (398-418) | R Q P V H Q L R - - F P L A R Q V L L E | SEQ. I.D. NO:32 |
| xFGFR4 | (CAA61930) | (424-444) | L Q T P T V H K L R - - F P L I R Q F L E E | SEQ. I.D. NO:33 |

METHODS OF INDENTIFYING MODULATORS OF THE FGF RECEPTOR

CROSS-REFERENCE TO RELATED APPLICATIONS

The present application is a Continuation application of U.S. application Ser. No. 09/757,415, filed Jan. 9, 2001, now U.S. Pat. No. 7,108,984 which is a non-provisional application claiming the priority of provisional U.S. Ser. No. 60/175, 867 filed Jan. 12, 2000, the disclosures of which are hereby incorporated by reference in their entireties. Applicants claim the benefits of these applications under 35 U.S.C. § 119(e) and § 120.

GOVERNMENTAL SUPPORT

The research leading to the present invention was supported, at least in part, by a grant from the National Institutes of Health, Grant No. GM59432-01. Accordingly, the Government may have certain rights in the invention.

FIELD OF THE INVENTION

The present invention provides the three-dimensional structure of a complex between the phosphotyrosine binding domain (PTB) of Suc 1-associated neurotrophic factor target protein (SNT) and the SNT binding site of the fibroblast growth factor receptor (FGFR). The three-dimensional structural information is included in the invention. The interaction between SNT and FGFR plays a key role in the regulation of cell proliferation. Therefore, the present invention provides procedures for identifying agents that can inhibit tumor proliferation through the use of rational drug design predicated on the three-dimensional data provided herein.

BACKGROUND OF THE INVENTION

The discovery and the extensive biochemical and biophysical characterization of the evolutionarily conserved cytoplasmic protein modular domains (such as SH2, SH3, PH, and WW domains) have revolutionized the way protein-protein interactions in cellular signal transduction is understood [Pawson and Scott, *Nature* 278: 2075-2080 (1997)]. Since these protein module-mediated interactions play an important role in regulating numerous cellular processes including cell growth, proliferation, differentiation and apoptosis, studies of the protein domain-mediated pathways have revealed the molecular basis of various human diseases. This has led to the discovery of new drug targets for treatment of these diseases.

The Phosphorylated Tyrosine Binding (PTB) domain (also called PID or SAIN domains) is another evolutionarily conserved cytoplasmic protein modular domain involved in cellular signal transduction. The PTB domain was first identified as a protein module that could bind phosphorylated tyrosines, and thus was classified as an alternative to the Src homology 2 (SH2) domain [Blaikie et al. *J. Biol. Chem.* 269:32031-32034 (1994); Kavanaugh, and Williams, *Science* 266:862-1865 (1994); O'Neill et al., *Mol. Cell. Biol.* 14: 6433-6442 (1994)]. However, PTB domains are structurally and functionally distinct from SH2 domains, and recognize amino acid residues amino-terminal (rather than carboxyl-terminal) to the phosphotyrosine (pY) [Zhou and Fesik, *S. W. Prog. Biophys. Molec. Biol.* 64:221-235 (1995)]. In particular, PTB domains preferentially bind to phosphorylated proteins at sites containing an NPXpY motif and hydrophobic amino acids amino-terminal to this sequence [Gustafson et al. *Mol. Cell. Biol.* 15:2500-2508 (1995); Kavanaugh et al. *Science* 268:1177-1179 (1995); Zhou et al., *J. Biol. Chem.* 270: 31119-31123 (1995); Trub et al., *J. Biol. Chem.* 270:18205-18208 (1995); Singyang, *J. Biol. Chem.* 270:14863-14866 (1995)]. Moreover, unlike SH2 domains, PTB domains typically show very low protein sequence homology. Different PTB domains exhibit distinct selectivity for residues amino-terminal to the NPXpY motif (SEQ ID NO:6). For example, the PTB domain of the insulin receptor substrate 1. (IRS-1) favors hydrophobic residues at different structural locations of its receptor, than those preferred by the PTB domain of the adaptor protein Shc. Recent studies demonstrate that the PTB domains of X11 and Numb can also recognize sequences related to the NPXpY motif in tyrosine-phosphorylation and non-phosphorylation-dependent manners [Li et al. *Proc. Natl. Acad. Sci. USA* 94: 7204-7209 (1997); Li et al. *Nat., Struct. Biol.* 5:1075-1083 (1998); and Zhang et al., *EMBO J.* 16:6141-6150 (1997)].

The NMR structural analyses of the Shc and IRS-1 PTB domains revealed the detailed structural basis of their protein recognition [Zhou et al., *Nature* 378:584-592 (1995); and Zhou et al, *Nature Struct. Biol.* 3:388-393 (1996)]. Despite their very low sequence homology, the PTB domains of Shc and IRS-1 consist of a conserved pleckstrin (PH) domain fold, i.e. a β-sandwich containing two nearly orthogonal, anti-parallel β-sheets capped at one end by an amphipathic C-terminal α-helix. Furthermore as stated above, the structurally related PTB domains of Shc and IRS-1 employ two very different mechanisms for recognizing the phosphotyrosine and the hydrophobic residues amino-terminal to the NPXpY sequence. For example, for Shc, an Ile residue of a synthetic peptide derived from TRKA receptor (HIIEN-PQpYFSDA, SEQ ID NO:7) binds in a deep hydrophobic pocket located between β5 and the C-terminal α-helix. The corresponding residue of a peptide derived from interleukin-4 receptor (IL-4R) (LVIAGNPApYRS, SEQ ID NO:4), binds on the surface of the protein. In addition, the IRS-1 PTB domain recognizes Ile and Leu of the IL-4R peptide through interactions with a hydrophobic site on the surface of a second β-sheet, whereas the analogous site in Shc is not available for peptide binding, because it is covered by a loop and the N-terminal portion of an α-helix. Notably, in contrast to SH2 domains, key arginines that are important for binding to phosphotyrosine are located in different regions of different PTB domain sequences. SNT (suc1-associated neurotrophic factor target protein) proteins are two newly discovered insulin receptor substrate-like (IRS-like) signaling adaptor molecules that are specifically activated by receptors for fibroblast growth factors (FGF), nerve growth factors (NGF), and glial-derived neurotrophic factor, but are not activated by most other growth factor receptor kinases [Xu et al., *J. Biol. Chem.* 273:17987-17990 (1998); Kouhara et al. *Cell* 89:693-702 (1997); Meakin et al., *J. Biol. Chem.* 274:9861-9870 (1999)]. SNT tyrosine phosphorylation promotes activation of Ras/MAPK and SHP-2, two biochemical pathways critical for ligand-induced biological responses. Current studies suggest that SNT activation enables FGFs and NGFs to elicit specific biological responses not achieved by activation of other receptor tyrosine kinases, which fail to stimulate SNTs. It has further been shown that the activation and tyrosine-phosphorylation of SNTs require direct contact between receptors and the amino-terminal phosphotyrosine binding domain of each SNT [Xu et al., *J. Biol. Chem.* 273:17987-17990 (1998); Meakin et al., *J. Biol. Chem.* 274:9861-9870 (1999)]. Whereas SNT PTB domains recognize a canonical NPXpY motif on NGF receptors such as TRKA, they unexpectedly bind a tyrosine- and asparagine-free motif in the juxtamembrane segment of the FGF receptor (FGFR). Thus, the SNT PTB domain represents a very unique protein modular domain, which can specifically bind two seemingly unrelated receptor peptide moieties.

The structural and functional diversity of PTB domains is further demonstrated in the SNT PTB domains. Sequence homology alignment and secondary prediction analysis using an approach of profile-based neural network predictions [PHD method; EMBL-Heidelberg et al., *Mol. Bol.* 232, 584-599 (1993); Rost and Sander, *Proteins* 19:55-77 (1994)] reveals that SNT PTB domains contain a large insert sequence (predicted to be an α-helix) located between the corresponding strand P7 and the C-terminal α-helix in the Shc and the IRS-1 PTB domains. It is interesting to note that whereas in all of the published three-dimensional structures of PTB and PH domains (regardless of whether they were determined by NMR or X-ray crystallography) structural variations have been found in different loop regions, none of have been observed between the P7 and the C-terminal α-helix region.

One means of modulating cellular proliferation and/or differentiation is to either inhibit or facilitate the interaction of the PTB domain of an SNT and the FGF receptor. Therefore, there is a need to identify agonists or antagonists to the SNT/FGFR complex. Unfortunately, such identification has heretofore relied on serendipity and/or systematic screening of large numbers of natural and synthetic compounds. A far superior method of drug-screening relies on structure based drug design. In this case, the three dimensional structure of SNT/FGFR complex is determined and potential agonists and/or potential antagonists are designed with the aid of computer modeling [Bugg et al., *Scientific American, December:* 92-98 (1993); West et al., *TIPS,* 16:67-74 (1995); and Dunbrack et al., *Folding & Design,* 2:27-42 (1997)]. However, heretofore the three-dimensional structure of the SNT/FGFR complex has remained unknown. Therefore, there is a need for obtaining a form of the SNT/FGFR complex that is amenable for NMR analysis and/or X-ray crystallographic analysis. Furthermore there is a need for the determination of the three-dimensional structure of such complexes. Finally, there is a need for procedures for related structural based drug design predicated on such structural data.

The citation of any reference herein should not be construed as an admission that such reference is available as "Prior Art" to the instant application.

SUMMARY OF THE INVENTION

The present invention provides the structure of a binding complex between the PTB domain of SNT-1 and a peptide derived from the SNT-1 binding site of the fibroblast growth factor receptor (FGFR). The structural information provided can be employed in methods of identifying drugs that can modulate cellular proliferation since the SNT-1/FGFR interaction plays a major role in the regulation of mitogenic cell signaling. In a particular embodiment, the three-dimensional structural information is used in the design of an inhibitor of cell proliferation. Such an inhibitor could be used as an anti-tumor agent.

The present invention also provides an isolated nucleic acid that encodes a polypeptide that comprises the amino acid residues 11-140 of SEQ ID NO:1. In a related embodiment the peptide comprises amino acid residues 11-140 of SEQ ID NO:1 with a conservative amino acid substitution.

The present invention also includes an isolated nucleic acid that encodes a peptide derived from FGFR1 consisting of 12 to 100 amino acids, preferably 16 to 50 amino acids and more preferably 20 to 30 amino acids which comprises the amino acid sequence of SEQ ID NO:5:

Val Xaa Xaa Leu Xaa Xaa Xaa Ile Xaa Leu Xaa Arg Xaa Val Xaa Val.

Preferably this peptide binds to the PTB domain of SNT1.

In another embodiment, the present invention provides an isolated nucleic acid that encodes a peptide derived from FGFR1 consisting of 12 to 100 amino acids, preferably 16 to 50 amino acids and more preferably 20 to 30 amino acids which comprises the amino acid sequence of SEQ ID NO:3. In a related embodiment the nucleic acid encodes a peptide that comprises the amino acid sequence of SEQ ID NO:3 with a conservative amino acid substitution. Again it is preferable that the peptide binds to the PTB domain of SNT1.

All of the nucleic acids of the present invention can be in an isolated form, and/or operatively linked to an expression control sequence. In addition, all of the nucleic acids of the present invention can further comprise a heterologous nucleotide sequence. Furthermore, all of the nucleic acids of the present invention operatively linked to an expression control sequence can be used to transform or transfect a unicellular host. The present invention also provides methods of expressing the peptides and proteins fragments of the present invention in the unicellular host. One such method comprises culturing the unicellular host in an appropriate cell culture medium under conditions that provide for the expression of the fragment and/or peptide by the cell. In addition, the present invention includes methods that further comprise the step of purifying the peptides and fragments. The purified forms of the fragments and peptides are also included as part of the present invention.

The present invention also provides an isolated polypeptide comprising amino acid residues 11-140 of SEQ ID NO:1. In a related embodiment the peptide comprises amino acid residues 11-140 of SEQ ID NO:1 with a conservative amino acid substitution.

The present invention also includes an isolated peptide derived from FGFR1 consisting of 12 to 100 amino acids, preferably 16 to 50 amino acids and more preferably 20 to 30 amino acids which comprises the amino acid sequence of SEQ ID NO:5:

Val Xaa Xaa Leu Xaa Xaa Xaa Ile Xaa Leu Xaa Arg Xaa Val Xaa Val.

Preferably this peptide binds to the PTB domain of SNT1.

In another embodiment, the present invention includes an isolated peptide derived from FGFR1 consisting of 12 to 100 amino acids, preferably 16 to 50 amino acids and more preferably 20 to 30 amino acids which comprises the amino acid sequence of SEQ ID NO:3. In a related embodiment the peptide comprises the amino acid sequence of SEQ ID NO:3 with a conservative amino acid substitution. Again it is preferable that the peptide binds to the PTB domain of SNT1. In a particular embodiment, the peptide has the amino acid sequence of SEQ ID NO:4.

The present invention also provides fusion proteins/peptides including chimeric proteins/peptides comprising the peptides and/or fragments of the present invention. All of the isolated peptides and/or fragments of the present invention, and all of the recombinant peptides and/or fragments of the present invention may be parts of these fusion and chimeric proteins/peptides. In one such embodiment, a fusion protein comprises the PTB domain of SNT-1 and the green fluorescent protein. In another such embodiment, the fusion protein comprises a FGFR derived peptide together with a FLAG tag. The present invention further provides methods of using the peptides and/or fragments of the present invention in a drug screening assay. Any of the peptides and/or fragments, and/or fusion proteins/peptides of the present invention may be used in such methods. The peptides or protein fragments of the present invention can also be labeled. In another such embodiment, the peptides and/or fragments can be bound to a solid support.

The present invention further provides assays for testing potential drugs that are selected/identified by the three-dimensional structural analysis of SNT/FGFR complex of the present invention, for the ability of the potential drug to interfere with the complex formation, for example.

The present invention further provides methods of identifying compounds or agents that modulate the stability of a SNT/FGFR complex and/or modulate the binding of SNT with FGFR. In one aspect of the present invention these methods employ the three-dimensional structure of the SNT/FGFR complex.

One such embodiment comprises selecting a potential compound by performing rational drug design with the set of atomic coordinates obtained from Tables 1-5. In a related embodiment the selection of the potential compound is performed by rational drug design after obtaining a set of atomic coordinates defining the three-dimensional structure of the SNT/FGFR complex consisting of a fragment of SNT consisting of amino acid residues 11-140 of SEQ ID NO:1 and a fragment of FGFR consisting of SEQ ID NO:3. Preferably the selecting is performed in conjunction with computer modeling. In either case, the potential compound is contacted with a SNT/FGFR complex comprising an SNT or an SNT fragment, and FGFR or an FGFR fragment, and the stability of the SNT/FGFR complex is determined (e.g., measured) in the presence of the compound. A potential compound is identified as a compound that modulates the stability of the SNT/FGFR complex when there is an change in the stability of the SNT/FGFR complex. The compound is identified as a stabilizer of the SNT/FGFR complex when the stability of the SNT/FGFR complex increases in its presence, whereas the compound is identified as a destabilizer of the SNT/FGFR complex when the stability of the SNT/FGFR complex decreases in its presence.

In another embodiment, the method identifies a compound or an agent that modulates the formation of a SNT/FGFR complex using the three-dimensional structure of the SNT/FGFR complex. One particular embodiment of this type comprises selecting a potential compound that binds to the PTB domain of SNT. In another embodiment, a potential compound is selected that binds to the SNT binding region of FGFR. Preferably the selection is performed using rational drug design with the set of atomic coordinates obtained from Tables 1-5. Alternatively, the selection of the potential compound is performed by rational drug design after obtaining a set of atomic coordinates defining the three-dimensional structure of the SNT/FGFR complex consisting of a fragment of SNT consisting of amino acid residues 11-140 of SEQ ID NO:1 and a fragment of FGFR consisting of SEQ ID NO:3. Preferably the selection is performed in conjunction with computer modeling. The potential compound is contacted with an SNT or an SNT fragment, and FGFR or an FGFR fragment under conditions in which the SNT/FGFR complex can form in the absence of the potential compound. The binding affinity of the SNT or the SNT fragment with FGFR or the FGFR fragment is then determined (e.g., measured) in the presence of the compound. A potential compound is identified as a compound that modulates the formation of the SNT/FGFR complex when there is a change in the binding affinity of the SNT or the SNT fragment with FGFR or the FGFR fragment. The compound is identified as an agonist of the formation of the SNT/FGFR complex when the binding affinity of the SNT/FGFR complex increases in its presence, whereas the compound is identified as an inhibitor of the formation of the SNT/FGFR complex when the binding affinity of the SNT/FGFR complex decreases in its presence.

The present invention further provides a method of selecting a compound or an agent that potentially modulates the SNT/FGFR dependent cellular signaling pathway. One such embodiment comprises defining the structure of the SNT/FGFR complex by the atomic coordinates obtained from Tables 1-5 and selecting a compound which potentially modulates the SNT/FGFR dependent cellular signaling pathway with the aid of the defined structure. In a related embodiment the selection of the potential compound is performed by rational drug design after obtaining a set of atomic coordinates defining the three-dimensional structure of the SNT/FGFR complex consisting of a fragment of SNT consisting of amino acid residues 11-140 of SEQ ID NO:1 and a fragment of FGFR consisting of SEQ ID NO:3. In one such embodiment the compound inhibits the SNT/FGFR dependent cellular signaling pathway, whereas in another embodiment the compound stimulates the SNT/FGFR dependent cellular signaling pathway.

The present invention further provides a method of selecting a compound that potentially binds to the PTB domain of SNT1 that comprises defining the structure of the SNT/FGFR complex by the atomic coordinates obtained from Tables 1-5. With the aid of the defined structure a compound is selected which potentially binds the PTB domain of SNT1. In a related embodiment the selection of the potential compound is performed by rational drug design after obtaining a set of atomic coordinates defining the three-dimensional structure of the SNT/FGFR complex consisting of a fragment of SNT consisting of amino acid residues 1-140 of SEQ ID NO:1 and a fragment of FGFR consisting of SEQ ID NO:3. In a related embodiment, a compound is selected that binds to the SNT binding region of FGFR. In another embodiment, the compound is selected to bind to the SNT/FGFR complex.

As anyone having skill in the art of drug development would readily understand, the potential drugs selected by the above methodologies can be refined by re-testing in appropriate drug assays, including those disclosed herein. Chemical analogs of such potential drugs can be obtained (either through chemical synthesis or drug libraries) and be analogously tested. Therefore, methods comprising successive iterations of the steps of the individual drug assays, as exemplified herein, using either repetitive or different binding studies, or transcription activation studies or other such studies are envisioned in the present invention. In addition, potential drugs may be identified first by rapid throughput drug screening, as described below, prior to performing computer modeling on a potential drug using the three-dimensional structure of the SNT/FGFR complex.

The present invention further comprises all of the potential, selected, and putative drugs as well as the drugs themselves identified by methods of the present invention. Accordingly, it is a principal object of the present invention to provide the three-dimensional coordinates of the SNT/FGFR complex.

It is a further object of the present invention to provide soluble fragments of SNT that comprise the PTB domain, and that can bind to FGFR.

It is a further object of the present invention to provide a soluble fragment of FGFR that comprises The binding site for the PTB of SNT.

It is a further object of the present invention to provide methods of identifying drugs that can modulate the SNT/FGFR interaction.

It is a further object of the present invention to provide methods of identifying drugs that can modulate cellular proliferation through modulating the SNT/FGFR interaction.

It is a further object of the present invention to provide methods that incorporate the use of rational design for identifying drugs that stabilize the SNT/FGFR complex.

It is a further object of the present invention to provide methods that incorporate the use of rational design for identifying drugs that inhibit the SNT/FGFR complex.

It is a further object of the present invention to provide detailed structural information regarding the binding of SNT and FGFR electronically, magnetically, or electromagnetically.

It is a further object of the present invention to provide a computer that comprises a representation of the three-dimensional structure of the SNT/FGFR binding complex and/or relevant portions thereof.

It is a further object of the present invention to provide methodologies for exploiting such structural information in order to develop potential anti-tumor drugs with the use of structure based rational drug design.

These and other aspects of the present invention will be better appreciated by reference to the following drawings and Detailed Description.

BRIEF DESCRIPTION OF THE DRAWINGS

FIGS. 1A-1B depict an alignment of protein sequence homology. FIG. 1A depicts the Sequence alignment of PTB domains of the SNT and IRS proteins. Amino acid sequence identifiers (SEQ ID Nos:8-33 and accession numbers of the proteins are indicated along the protein sequences. Protein sequences of FRS2α and FRS2β have been reported [Ong et al., *Mol. Cell. Biol.* 20:979-989 (2000)]. The experimentally determined secondary structure elements are displayed above or below the sequences of the PTB domains of SNTs or IRSs [Zhou et al., *Nat. Struc. Biol.* 3:388-393 (1996)], respectively. Asterisks highlight residues in the SNT-1 PTB domain that show intermolecular NOEs to the hFGFR1 peptide. Absolutely or highly conserved residues among the SNT and IRS PTB domains are shown in red and blue, respectively. Two underlined Arg residues of SNT-1 were both changed by site-directed mutagenesis to Gln. Arrows indicate constructs used in truncation analysis of SNT-1 PTB domain binding to hFGFR1 or TRK. Pro residues located C-terminal to the SNT-1 PTB domain are shown in bold. FIG. 1B depicts the Sequence alignment of the juxtamembrane region of the FGFR family. For each FGFR group (FGFR1-4), protein sequences from three representative species, i.e., human, mouse, and xenopus, are selected. The number of observed intermolecular NOEs identified for a particular amino acid residue of the hFGFR1 peptide is shown in red above the sequence. Absolutely or highly conserved residues are highlighted in yellow and blue background, respectively.

FIG. 2A shows the stereoview of the backbone atom superposition of the final 20 NMR-derived structures of the complex, containing the SNT-1 PTB domain residues 18-116 and the hFGFR1 peptide residues 411-430. The terminal residues, which are structurally disordered, are omitted for clarity. For the final 20 structures, the root-mean-square deviations (RMSDs) of the backbone and all heavy atoms for protein residues 18-116 are 0.74±0.16 Å and 1.46±0.16 Å, respectively. The corresponding RMSDs for the protein secondary structure regions (protein residues 19-24, 35-40, 45-49, 52-57, 63-68, 71-76, 85-90, 94-107 and 111-115) are 0.40±0.05 Å and 0.88±0.05 Å, respectively. The RMSDs of the backbone and all heavy atoms for the hFGFR1 peptide (residues 412-430) are 0.56±0.10 Å and 1.25±0.15 Å, respectively. FIG. 2B is a ribbon depiction of the averaged minimized NMR structure of the SNT-1 PTB domain/hFGFk1 complex. The orientation of FIG. 2B is as shown in FIG. 2A. FIG. 2C is a ribbon diagram of the SNT-1 PTB domain structure from the top of the protein, which is rotated ~90° from the orientation in FIG. 2B. FIG. 2D is a molecular surface representation of the SNT-1 PTB domain structure calculated in GRASP [Nicholls et al., *Biophys. J.* 64:166-170 (1993)]. The protein is color-coded by surface curvature, and the color gradient from green to dark gray reflects decreasing solvent exposure. The hFGFR1 peptide molecule is shown as a ball and stick representation color-coded by atom-type.

FIG. 4 depicts the secondary structure of the intermolecular antiparallel β-sheet of the complex. The number of intermolecular NOEs observed in $^{13}C$- or $^{15}N$-edited ($F_1$), $^{13}C/^{15}N$-filtered ($F_3$) 3D NOESY spectra is summarized for individual amino acid residue. NOEs that define the structure of the β-sheet are indicated by arrows. Arrows for intramolecular, $^{13}C$-based and 15N-based intermolecular NOEs, are color-coded in black, green and red, respectively. Broken lines (blue) highlight two intermolecular hydrogen bonds that are supported by amide exchange data. The intermolecular interactions are depicted for three-regions of the hFGFR1 peptide (green). FIG. 4B depicts the C-terminal (residues 424-430) region. The side-chains of the protein and the peptide residues are displayed in orange and blue, respectively. FIG. 4C shows the middle (residues 417-423) region. The three loops connecting β1/β2, β3/β4 and β6/β7 that form a hydrophobic binding pocket for binding to the peptide residue Val-414 are colored in pink. FIG. 4D shows the N-terminal (residues 409-416) region. FIG. 4E depicts the complementary electrostatic interactions between the SNT-1 PTB domain and hFGFR1 peptide residues.

FIG. 6A shows the effect of hFGFR1 point mutations on interactions with the SNT-1 PTB domain, determined by yeast two-hybrid binding assays. Data for peptide mutants are calculated from an average of 5 independent experiments. Western blot showing BD fusion protein expression of wild type and mutant hFGFR1 in the yeast cells. FIG. 6B shows the structure of the SNT-1 PTB domain/hFGFR1 complex showing location of Arg-63 and Arg-78 (blue) that are essential for binding to the phosphotyrosine in the NPXpY motif. The backbone of the hFGFR1 peptide is shown in green. The distinct β8 strand of the SNT-1 PTB domain is displayed in red. FIG. 6C depicts the structure of the IRS-1 PTB domain in complex with a tyrosine-phosphorylated peptide derived from interleukin-4 receptor (LVIAGNPApYRS, residues 489-499) determined by NMR [Zhou et al., *Nat. Struc, Biol.* 3:388-393 (1996)]. The peptide residues are shown in green, and the two key Arg residues (Arg-212 and Arg-227) of the PTB domain that are essential for phosphotyrosine binding are displayed in blue. FIG. 6D shows the results of a yeast two-hybrid binding studies of SNT-1 β8 truncation effect on its interactions with hFGFR1 and tyrosine-phosphorylated TRKB. The panel framed in red shows the loss of interaction between hFGFR1 and the SNT-1 PTB domain protein lacking the β8 strand. Colony formation on the synthetic complete medium lacking Leu and Trp (Leu$^-$, Trp$^-$) illustrates the efficiency of co-transformation with the two plasmids, while growth on the corresponding medium lacking His, Leu and Trp (His$^-$, Leu$^-$, Trp$^-$) shows level of protein-protein interaction.

DETAILED DESCRIPTION OF THE INVENTION

Figure 2A:
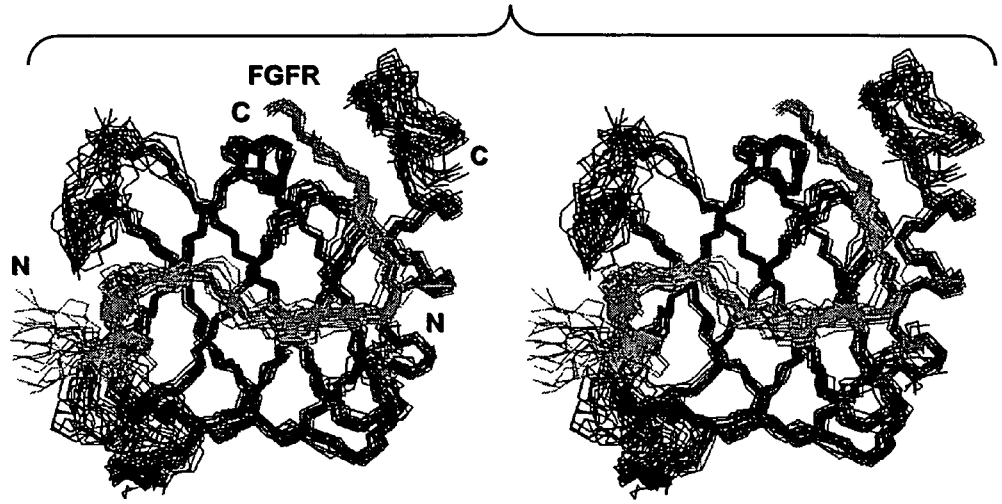
FIGS. 2A-2D depict the structure of the SNT-1 PTB domain/hFGFR1 complex.

The present invention provides the first detailed structural information regarding the complex of the PTB domain of SNT-1 with a peptide derived from the known SNT-1 binding site of the fibroblast growth factor receptor (FGFR). The present invention therefore provides the three-dimensional structure of the SNT-1 PTB domain/FGFR complex. Since the SNT-1/FGFR interaction plays a significant role in the regulation of mitogenic cell signaling, the structural information provided herein can be employed in methods of identifying drugs that can modulate the proliferation of cells. In a particular embodiment, the three-dimensional structural information is used in the design of an inhibitor of cell proliferation for the treatment of cancer.

The three-dimensional structure of the SNT-1 PTB domain/FGFR complex disclosed herein demonstrates that the interaction between the PTB domain of SNT-1 and FGFR differs significantly from the manner that PTB domains have been reported to interact with the canonical NPXpY motif (where X is any amino acid and pY is a phosphorylated tyrosine). Furthermore, the structural information disclosed herein provides the basis for mutational analysis of the SNT-1 PTB/FGFR complex. Key amino acid residues from both SNT-1 and FGFR that are essential for the protein-protein recognition are also identified.

SNT-1 also plays a role in regulating nerve growth factor (NGF) receptor signaling via its binding through its PTB domain with the activated/tyrosine phosphorylated NGF receptor. As stated above this interaction differs significantly with that disclosed herein for the SNT/FGFR complex. Based on the new structural information, the key amino acid residues for the binding of the SNT1-PTB domain with the NGF TRKA receptor can be identified and further elucidated using basic mutagenesis and standard isothermal titration calorimetry. The results obtained from the structural and functional studies disclosed herein indicate that there is a novel mechanism through which SNT proteins regulate neuronal cell growth and differentiation. Such detailed structural and mechanistic findings provide the foundation for structure-based rational drug design. The agents identified by this procedure will be useful for ameliorating conditions involving the dysfunction of cell signaling pathways involving the NGF receptor and the FGF receptor. More particularly, FGFRs have been implicated to play a causal role in the development of the following human ailments such as in tumorigenesis including various forms of human cancer, and in skeletal disorders, such as Achondroplasia, hypochondroplasia, Crouzon syndrome, Apert syndrome, and Pfeiffer syndrome.

Structure based rational drug design is the most efficient method of drug development. However, heretofore, little information has been disclosed regarding the structure of the SNT/FGFR interaction. Obtaining detailed structural information requires an extensive NMR or X-ray crystallographic analysis. In the former case, the entire SNT-1/FGFR complex has a molecular weight which is beyond the present capabilities of NMR analysis. In the latter case, crystallography of proteins remains a black art. The present invention overcomes the difficulties described above, by providing fragments of the SNT-1/FGFR complex (identified below) that retain the necessary structural elements for binding. Such SNT-1/FGFR complexes are amenable to NMR structural analysis. By determining and then exploiting the detailed structural information of this complex (exemplified by NMR analysis below) the present invention provides novel methods for developing new anti-tumor drugs through structure based rational drug design.

Thus the present invention provides a representative set of structural coordinates for the SNT-1 PTB domain/FGFR peptide complex (Table 1) which were obtained by NMR analysis. A Ribbon diagrams of the three-dimensional structure of the SNT-1 PTB domain in complex with the FGFR peptide is shown in FIGS. 2 and 4. The present invention also provides the NOE-derived distance restraints, and NMR chemical shift assignments of the SNT-1 PTB domain/FGFR peptide. The NMR chemical shift assignments of the SNT-1 PTB domain/FGFR peptide complex are included in the chemical shift table (Table 2) for the $^1$H-$^{15}$N HSQC spectrum of SNT-1 PTB domain/FGFR peptide complex. Tables 3-5 contain the NMR experimentally determined distance restraints that are used in the structural calculations, including the hydrogen bond distance restraints (Table 3), the unambiguous distance restraints (Table 4) and the ambiguous distance restraints (Table 5). The sample coordinates data set of Table 1, the chemical shifts of Table 2, along with the information contained in Tables 3-5 are sufficient to enable the skilled artisan to practice the invention. In addition, Tables 1-5 are also capable of being placed into a computer readable form which is also part of the present invention. Furthermore, methods of using these coordinates and chemical shifts and related information (including in computer readable forms) in drug assays are disclosed. More particularly, such coordinates can be used to identify potential ligands or drugs which will modulate the binding of the SNT with FGFR. Since the SNT/FGFR interaction is naturally stimulated by FGF and leads to the activation of cell proliferation agents such as Ras, compounds that inhibit the SNT FGFR binding will act to inhibit cellular proliferation at a comparatively early stage of the signal transduction pathway. Similarly, compounds that act as agonists for the SNT FGFR interaction will act as agonists for cellular proliferation.

In addition, the present invention provides a computer that comprises a representation of the SNT/FGFR binding complex in computer memory that can be used to screen for compounds that will enhance or alternatively inhibit the binding of SNT to FGFR. In a related embodiment, the computer can be used in the design of altered SNT and/or FGFR proteins that have either enhanced, or alternatively diminished binding affinity for each other. Preferably, the computer comprises portions or all of the information contained in Tables 1-5. In a particular embodiment, the computer comprises: (i) a machine-readable data storage material encoded with machine-readable data, (ii) a working memory for storing instructions for processing the machine readable data, (iii) a central processing unit coupled to the working memory and the machine-readable data storage material for processing the machine-readable data into a three-dimensional representation, and (iv) a display coupled to the central processing unit for displaying the three-dimensional representation.

Figure 5:
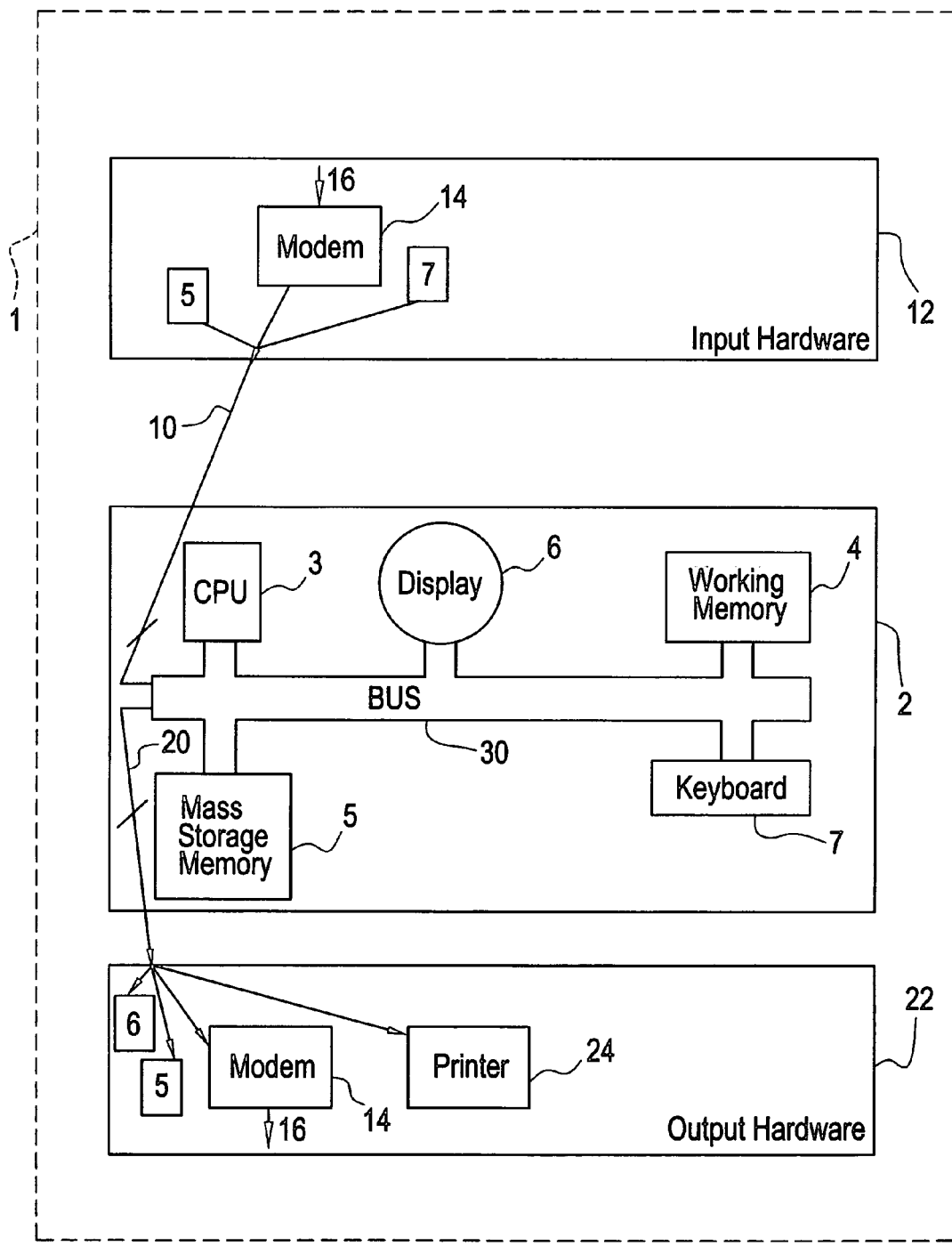
FIG. 5 depicts a schematic of a computer comprising a central processing unit ("CPU"), a working memory, a mass storage memory, a display terminal, and a keyboard that are interconnected by a conventional bidirectional system bus. The computer can be used to display and manipulate the structural data of the present invention.

Thus the machine-readable data storage medium comprises a data storage material encoded with machine readable data which can comprise portions or all of the structural information contained in Tables 1-5. One embodiment for manipulating and displaying the structural data provided by the present invention is schematically depicted in FIG. 5. As depicted the System 1, includes a computer 2 comprising a central processing unit ("CPU") 3, a working memory 4 which may be random-access memory or "core" memory, mass storage memory 5 (e.g., one or more disk or CD-ROM drives), a display terminal 6 (e.g., a cathode-ray tube), one or more keyboards 7, one or more input lines 10, and one or more output lines 20, all of which are interconnected by a conventional bidirectional system bus 30.

Input hardware 12, coupled to the computer 2 by input lines 10, may be implemented in a variety of ways. Machine-readable data may be inputted via the use of one or more modems 14 connected by a telephone line or dedicated data line 16. Alternatively or additionally, the input hardware 12 may comprise CD-ROM or disk drives 5. In conjunction with the display terminal 6, the keyboard 7 may also be used as an input device. Output hardware 22, coupled to computer 2 by output lines 20, may similarly be implemented by conventional devices. Output hardware 22 may include a display terminal 6 for displaying the three dimensional data. Output hardware might also include a printer 24, so that a hard copy output may be produced, or a disk drive 5, to store system output for later use, see also U.S. Pat. No. 5,978,740, Issued Nov. 2, 1999, the contents of which are hereby incorporated by reference in their entireties.

In operation, the CPU 3 (i) coordinates the use of the various input and output devices 12 and 22; (ii) coordinates data accesses from mass storage 5 and accesses to and from working memory 4; and (iii) determines the sequence of data processing steps. Any of a number of programs may be used to process the machine-readable data of this invention.

Therefore, if appearing herein, the following terms shall have the definitions set out below.

As used herein the term "SNT-1 PTB domain/FGFR peptide complex" is used interchangeably with the term "SNT/FGFR complex" and the term "SNT-FGFR complex" are all meant to denote a binding complex between the PTB domain of SNT or portion thereof that binds to the FGF receptor, and a fragment of the FGF receptor that binds to the PTB domain of SNT. One such a complex is identified in the Example below.

As used herein the term "SNT/FGFR dependent cellular signaling pathway" is a cellular signaling pathway in which the direct interaction between SNT and the FGF receptor (i.e., binding) is involved in transmitting the signal from an extracellular ligand for the receptor to the nucleus of the cell.

A "polypeptide" comprising a fragment of FGFR or SNT (or more particularly the SNT PTB domain) as used herein can be the "fragment" alone, or a larger chimeric or fusion peptide/protein which contains the "fragment".

As used herein a polypeptide or peptide "consisting essentially of" or that "consists essentially of" a specified amino acid sequence is a polypeptide or peptide that retains the general characteristics, e.g., activity of the polypeptide or peptide having the specified amino acid sequence and is otherwise identical to that protein in amino acid sequence except it consists of plus or minus 10% or fewer, preferably plus or minus 5% or fewer, and more preferably plus or minus 2.5% or fewer amino acid residues.

As used herein the terms "fusion protein" and "fusion peptide" are used interchangeably and encompass "chimeric proteins and/or chimeric peptides" and fusion "intein proteins/peptides". A fusion protein of the present invention can comprises a portion of an SNT or FGFR of the present invention joined via a peptide bond to at least a portion of another protein or peptide including a second SNT or FGFR protein in a chimeric fusion protein. For example fusion proteins can comprise a marker protein or peptide, or a protein or peptide that aids in the identification and/or monitoring of an SNT or FGFR peptide/protein of the present invention.

As used herein the terms "approximately" and "about" are used to signify that a value is within ten percent of the indicated value i.e., a protein fragment containing "approximately" 140 amino acid residues can contain between 126 and 154 amino acid residues.

As used herein the term "binds to" is meant to include all such specific interactions that result in two or more molecules showing a preference for one another relative to some third molecule. This includes processes such as covalent, ionic, hydrophobic and hydrogen bonding but does not include non-specific associations such solvent preferences.

As used herein, and unless otherwise specified, the terms "agent", "potential drug", "test compound" or "potential compound" are used interchangeably, and refer to chemicals which potentially have a use as an inhibitor or activator/stabilizer of SNT/FGFR binding, and preferably include drugs for the treatment or prevention of a disease and/or condition involving the FGF receptor. Therefore, such "agents", "potential drugs", and "potential compounds" may be used, as described herein, in drug assays and drug screens and the like.

As used herein a "small organic molecule" is an organic compound [or organic compound complexed with an inorganic compound (e.g., metal)] that has a molecular weight of less than 3 Kilodaltons.

As used herein, the term "gene" refers to an assembly of nucleotides that encode a polypeptide, and includes cDNA and genomic DNA nucleic acids.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogues thereof such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk; and no formamide; or 30%, formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-10.51). For hybridization with shorter nucleic acids, i.e., oligonucleotides, the position of mismatches becomes more important, and the length of the oligonucleotide determines its specificity (see Sambrook et al., supra, 11.7-1 1.8). Preferably a minimum length for a hybridizable nucleic acid is at least about 12 nucleotides; preferably at least about 18 nucleotides; and more preferably the length is at least about 27 nucleotides; and most preferably 36 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C. Preferably the wash and hybridization (binding) steps are identical.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences and synthetic DNA sequences. If the coding sequence is intended for expression in a eukaryotic cell, a polyadenylation signal and transcription termination sequence will usually be located 3' to the coding sequence. Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

As used herein, the term "homologous" in all its grammatical forms refers to the relationship between proteins that possess a "common evolutionary origin," including proteins from superfamilies (e.g., the immunoglobulin superfamily) and homologous proteins from different species (e.g., myosin light chain, etc.) [Reeck et al., Cell, 50:667 (1987)]. Such proteins have sequence homology as reflected by their high degree of sequence similarity.

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Similarly, in a particular embodiment, two amino acid sequences are "substantially homologous" or "substantially similar" when greater than 25% of the amino acids are identical (preferably at least about 50%, more preferably at least about 75%, and most preferably at least about 90 or 95% identical), or greater than about 60% (preferably at least about 75%, more preferably at least about 90%, and most preferably at least about 95 or 100%) are functionally identical. The sequence comparison is performed over a contiguous block of amino acid residues comprised by SNT, for example. In a preferred embodiment selected deletions or insertions that could otherwise alter the correspondence between the two amino acid sequences are taken into account. Preferably standard computer analysis is employed for the determination that is comparable, (or identical) to that determined with an Advanced Blast search at www.ncbi.nlm.nih.gov under the default filter conditions [e.g., using the GCG (Genetics Computer Group, Program Manual for the GCG Package, Version 7, Madison, Wisc.) pileup program using the default parameters].

As used herein an amino acid sequence is 100% "homologous" to a second amino acid sequence if the two amino acid sequences are identical, and/or differ only by neutral or conservative substitutions as defined below. Accordingly, an amino acid sequence is 50% "homologous" to a second amino acid sequence if 50% of the two amino acid sequences are identical, and/or differ only by neutral or conservative substitutions.

The term "corresponding to" is used herein to refer similar or homologous sequences, whether the exact position is identical or different from the molecule to which the similarity or homology is measured. Thus, the term "corresponding to" refers to the sequence similarity, and not the numbering of the amino acid residues or nucleotide bases.

As used herein a "heterologous nucleotide sequence" is a nucleotide sequence that is added to a nucleotide sequence of the present invention by recombinant methods to form a nucleic acid which is not naturally formed in nature. Such nucleic acids can encode fusion proteins or peptides, including chimeric proteins and peptides. Thus the heterologous nucleotide sequence can encode peptides and/or proteins which contain regulatory and/or structural properties. In another such embodiment the heterologous nucleotide can encode a protein or peptide that functions as a means of detecting the protein or peptide encoded by the nucleotide sequence of the present invention after the recombinant nucleic acid is expressed. In still another such embodiment the heterologous nucleotide can function as a means of detecting a nucleotide sequence of the present invention. A heterologous nucleotide sequence can comprise non-coding sequences including restriction sites, regulatory sites, promoters and the like.

General Techniques for Constructing Nucleic Acids that Express the SNT or FGFR Fragments of the Present Invention.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

The present invention also relates to cloning vectors containing nucleic acids encoding analogs and derivatives of the SNT and FGFR fragments of the present invention, including modified fragments, that have the same or homologous functional activity as the individual fragments, and homologs thereof The production and use of derivatives and analogs related to the fragments are within the scope of the present invention.

Due to the degeneracy of nucleotide coding sequences, other DNA sequences which encode substantially the same amino acid sequence as a nucleic acid encoding an FGFR fragment or peptide, or SNT PTB domain of the present invention may be used in the practice of the present invention. These include but are not limited to allelic genes, homologous genes from other species, which are altered by the substitution of different codons that encode the same amino acid residue within the sequence, thus producing a silent change. Likewise the FGFR fragments or peptides, or SNT PTB domains of the invention include, but are not limited to, those containing, as a primary amino acid sequence, analogous portions of their respective amino acid sequences including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, and lysine. The negatively charged (acidic) amino acids include aspartic acid and glutamic acid.

Particularly preferred conserved amino acid exchanges are:

(a) Lys for Arg or vice versa such that a positive charge may be maintained;
(b) Glu for Asp or vice versa such that a negative charge may be maintained;
(c) Ser for Thr or vice versa such that a free —OH can be maintained;
(d) Gln for Asn or vice versa such that a free $NH_2$ can be maintained;
(e) Ile for Leu or for Val or vice versa as roughly equivalent hydrophobic amino acids; and
(f) Phe for Tyr or vice versa as roughly equivalent aromatic amino acids.

A conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein. Specific amino acid residues for both the SNT and the FGFR fragments have been identified that are important for binding, indicating a lower stringency for the substitution of the remaining amino acids residues.

All of the FGFR and SNT PTB domain peptides/fragments of the present invention can be modified by being placed in a fusion or chimeric peptide or protein, or labeled e.g., to have an N-terminal FLAG-tag, or His6 tag. In a particular embodiment the SNT PTB domain fragment can be modified to contain a marker protein such as green fluorescent protein as described in U.S. Pat. No. 5,625,048 filed Apr. 29, 1997 and WO 97/26333, published Jul. 24, 1997 each of which are hereby incorporated by reference herein in their entireties.

The nucleic acids encoding peptides and protein fragments of the present invention and analogs thereof can be produced by various methods known in the art. The manipulations which result in their production can occur at the gene or protein level [Sambrook et al., 1989, supra]. The nucleotide sequence can be cleaved at appropriate sites with restriction endonuclease(s), followed by further enzymatic modification if desired, isolated, and ligated in vitro. In addition a nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis [Hutchinson et al., *J. Biol. Chem.*, 253:6551 (1978); Zoller and Smith, DNA, 3:479-488 (1984); Oliphant et al., *Gene*, 44:177 (1986); Hutchinson et al., *Proc. Natl. Acad. Sci. U.S.A.*, 83:710 (1986)], use of TAB® linkers (Pharmacia), etc. PCR techniques are preferred for site directed mutagenesis [see Higuchi, 1989, "Using PCR to Engineer DNA", in *PCR Technology: Principles and Applications for DNA Amplification*, H. Erlich, ed., Stockton Press, Chapter 6, pp. 61-70].

The identified and isolated nucleic acids can then be inserted into an appropriate cloning vector. A large number of vector-host systems known in the art may be used.

Protein Expression and Purification

A bacterial protein expression system can be used to make various stable isotopically labeled ($^{13}C$, $^{15}N$, and $^2H$) protein samples that are useful for a three-dimensional NMR structural determination of a protein complex. For example a pET15b (Novagen) bacterial expression vector can be constructed which expresses the recombinant SNT-1 PTB domain as an amino-terminal His-tagged fusion protein.

Protein expression and purification can be conducted using standard procedures for His-tagged proteins [Zhou et al., *J. Biol. Chem.* 270:31119-31123 (1995)]. To optimize the level of protein expression, various bacterial growth and expression conditions can be screened, which include different *E. Coli* cell lines, and growth and protein induction temperatures. Generally, it is preferred to obtain the maximum amount of soluble protein while still inducing protein expression with a relatively low IPTG concentration e.g., ~0.2 mM (final concentration) at 16° C. Under these conditions, reasonable quantities of protein were obtained (5-10 mg/ml of soluble protein) using the His-tagged plasmid transformed in *E. Coli* BL21 (DE3) cells grown in M9 minimal medium. The N-terminal His-tag can be readily cleaved with the treatment of protease thrombin in a 20 mM Tris buffer of pH 8.0 containing 200 mM NaCl and 5 mM P-Mercapto-ethanol.

One major advantage of using the heteronuclear multidimensional approach, as exemplified herein, is that the NMR resonance assignments of a protein are obtained in a sequence-specific manner which assures accuracy and greatly facilitates data analysis and structure determination [Clore, and Gronenborn, *Meth. Enzymol.* 239:249-363 (1994)]. In addition, the signal overlapping problems in the protein spectra are minimized by the use of multidimensional NMR spectra, which separates the proton signals according to the chemical shifts of their attached hetero-nuclei (such as $^{15}N$ and $^{13}C$). This NMR approach has been proven very powerful for structural analysis of large proteins [Clore and Gronenbom, *Meth. Enzymol.* 239:249-363 (1994)]. To facilitate sequence-specific resonance assignments for the structural study, a uniformly $^{13}C$, $^{15}N$-labeled and fractionally (75%) deuterated protein sample of the SNT-1 PTB domain can be prepared by growing bacterial cells in 75% $^2H_2O$. Such protein samples can be used for triple-resonance NMR experiments. A triple-labeled protein sample is useful for high-resolution NMR structural studies. Because of the favorable $^1H$, $^{13}C$, and $^{15}N$ relaxation rates caused by the partial deuteration of the protein, constant-time triple-resonance NMR spectra can be acquired with higher digital resolution and sensitivity [Sattler and Fesik, *Structure* 4:1245-1249 (1996)]. In addition, various stable-isotopically labeled ($^{15}N$ and $^{13}C$/$^{15}N$) proteins can also be prepared using this procedure.

Synthetic Polypeptides

The term "polypeptide" is used in its broadest sense to refer to a compound of two or more subunit amino acids, amino acid analogs, or peptidomimetics. The subunits are linked by peptide bonds. The FGFR peptides of the present invention may be chemically synthesized.

In addition, potential drugs or agents that may be tested in the drug screening assays of the present invention may also be chemically synthesized. Synthetic polypeptides, prepared using the well known techniques of solid phase, liquid phase, or peptide condensation techniques, or any combination thereof, can include natural and unnatural amino acids. Amino acids used for peptide synthesis may be standard Boc ($N^\alpha$-amino protected $N^\alpha$-t-butyloxycarbonyl) amino acid resin with the standard deprotecting, neutralization, coupling and wash protocols of the original solid phase procedure of Merrifield [*J. Am. Chem. Soc.*, 85:2149-2154 (1963)], or the base-labile $N^\alpha$-amino protected 9-fluorenylmethoxycarbonyl (Fmoc) amino acids first described by Carpino and Han [*J. Org. Chem.*, 37:3403-3409 (1972)]. Both Fmoc and Boc $N^\alpha$-amino protected amino acids can be obtained from Fluka, Bachem, Advanced Chemtech, Sigma, Cambridge Research Biochemical, Bachem, or Peninsula Labs or other chemical companies familiar to those who practice this art. In addition, the method of the invention can be used with other $N^\alpha$-protecting groups that are familiar to those skilled in this art. Solid phase peptide synthesis may be accomplished by techniques familiar to those in the art and provided, for example, in Stewart and Young [Solid Phase Synthesis, Second Edition, Pierce Chemical Co., Rockford, Ill. (1984)] and Fields and Noble [*Int. J. Pept. Protein Res.*, 35:161-214 (1990)], or using automated synthesizers, such as sold by ABS. Thus, polypeptides of the invention may comprise D-amino acids, a combination of D- and L-amino acids, and various "designer" amino acids (e.g., β-methyl amino acids, Cα-methyl amino acids, and Nα-methyl amino acids, etc.) to convey special properties. Synthetic amino acids include ornithine for lysine, fluorophenylalanine for phenylalanine, and norleucine for leucine or isoleucine. Additionally, by assigning specific amino acids at specific coupling steps, α-helices, β turns, β sheets, γ-turns, and cyclic peptides can be generated.

In a further embodiment, subunits of peptides that confer useful chemical and structural properties will be chosen. For example, peptides comprising D-amino acids will be resistant to L-amino acid-specific proteases in vivo. In addition, the present invention envisions preparing peptides that have more well defined structural properties, and the use of peptidomimetics, and peptidomimetic bonds, such as ester bonds, to prepare peptides with novel properties. In another embodiment, a peptide may be generated that incorporates a reduced peptide bond, i.e., $R_1$—$CH_2$—$NH$—$R_2$, where $R_1$ and $R_2$ are amino acid residues or sequences. A reduced peptide bond may be introduced as a dipeptide subunit. Such a molecule would be resistant to peptide bond hydrolysis, e.g., protease activity. Such peptides would provide ligands with unique function and activity, such as extended half-lives in vivo due to resistance to metabolic breakdown, or protease activity. Furthermore, it is well known that in certain systems constrained peptides show enhanced functional activity [Hruby, Life Sciences, 31:189-199 (1982); Hruby et al., Biochem J., 268:249-262 (1990)]; the present invention provides a method to produce a constrained peptide that incorporates random sequences at all other positions.

Constrained and cyclic peptides. A constrained, cyclic or rigidized peptide may be prepared synthetically, provided that in at least two positions in the sequence of the peptide an amino acid or amino acid analog is inserted that provides a chemical functional group capable of crosslinking to constrain, cyclise or rigidize the peptide after treatment to form the crosslink. Cyclization will be favored when a turn-inducing amino acid is incorporated. Examples of amino acids capable of crosslinking a peptide are cysteine to form disulfides, aspartic acid to form a lactone or a lactam, and a chelator such as γ-carboxyl-glutamic acid (Gla) (Bachem) to chelate a transition metal and form a cross-link. Protected γ-carboxyl glutamic acid may be prepared by modifying the synthesis described by Zee-Cheng and Olson [Biophys. Biochein. Res. Commun., 94:1128-1132(1980)]. A peptide in which the peptide sequence comprises at least two amino acids capable of crosslinking may be treated, e.g., by oxidation of cysteine residues to form a disulfide or addition of a metal ion to form a chelate, so as to crosslink the peptide and form a constrained, cyclic or rigidized peptide.

The present invention provides strategies to systematically prepare cross-links. For example, if four cysteine residues are incorporated in the peptide sequence, different protecting groups may be used (Hiskey, in The Peptides: Analysis, Synthesis, Biology, Vol. 3, Gross and Meienhofer, eds., Academic Press: New York, pp. 137-167 (1981); Ponsanti et al., Tetrahedron, 46:8255-8266 (1990)]. The first pair of cysteines may be deprotected and oxidized, then the second set may be deprotected and oxidized. In this way a defined set of disulfide cross-links may be formed. Alternatively, a pair of cysteines and a pair of chelating amino acid analogs may be incorporated so that the cross-links are of a different chemical nature.

Non-classical amino acids that induce conformational constraints. The following non-classical amino acids may be incorporated in the peptide in order to introduce particular conformational motifs: 1,2,3,4-tetrahydroisoquinoline-3-carboxylate [Kazmierski et al., J. Am. Chem. Soc., 113:2275-2283 (1991)]; (2S,3S)-methyl-phenylalanine, (2S,3R)-methyl-phenylalanine, (2R,3S)-methyl-phenylalanine and (2R, 3R)-methyl-phenylalanine (Kazmierski and Hruby, Tetrahedron Lett. (1991)]; 2-aminotetrahydronaphthalene-2-carboxylic acid [Landis, Ph.D. Thesis, University of Arizona (1989)]; hydroxy-1,2,3,4-tetrahydroisoquinoline-3-carboxylate [Miyake et al. J. Takeda Res. Labs., 43:53-76 (1989)]; β-carboline (D and L) [Kazmierski, Ph.D. Thesis, University of Arizona (1988)]; HIC (histidine isoquinoline carboxylic acid) [Zechel et al., Int. J. Pep. Protein Res., 43 (1991)]; and HIC (histidine cyclic urea) (Dharanipragada).

The following amino acid analogs and peptidomimetics may be incorporated into a peptide to induce or favor specific secondary structures: LL-Acp (LL-3-amino-2-propenidone-6-carboxylic acid), a β-turn inducing dipeptide analog [Kemp et al., J. Org. Chem., 50:5834-5838 (1985)]; β-sheet inducing analogs [Kemp et al, Tetrahedron Lett., 29:5081-5082 (1988); β-turn inducing analogs [Kemp et al., Tetrahedron Lett., 29:5057-5060 (1988)]; ∝-helix inducing analogs (Kemp et al., Tetrahedron Lett., 29:4935-4938 (1988)]; γ-turn inducing analogs [Kemp et al., J. Org. Chem., 54:109:115 (1989)]; and analogs provided by the following references: Nagai and Sato, Tetrahedron Lett., 26:647-650 (1985); DiMaio et al., J. Chem. Soc. Perkin Trans., p. 1687 (1989); also a Gly-Ala turn analog [Kahn et al., Tetrahedron Lett., 30:2317 (1989)]; amide bond isostere [Jones et al., Tetrahedron Lett., 29:3853-3856 (1988)]; tretrazol [Zabrocki et al., J. Am. Chem. Soc., 110:5875-5880 (1988)]; DTC [Samanen et al., Int. J. Protein Pep. Res., 35:501:509 (1990)]; and analogs taught in Olson et al., J. Am. Chem. Sci., 112:323-333 (1990) and Garvey et al., J. Org. Chem., 56:436 (1990). Conformationally restricted mimetics of beta turns and beta bulges, and peptides containing them, are described in U.S. Pat. No. 5,440,013, issued Aug. 8, 1995 to Kahn.

Structure-Based Mutation Analysis

Protein structural analysis using NMR spectroscopy has several unique advantages. In addition to high-resolution three-dimensional structural information, the chemical shift assignments for the protein obtained in the structural study further provides a map of the entire protein at the atomic level, which can be used for structure-based biochemical analysis of protein-protein interactions. For example, the information generated from the NMR structural analysis can also serve to identify specific amino acid residues in the peptide-binding site for complementary mutagenesis studies. Specific focus can be placed on those residues that display long-range NOEs (particularly the side-chain NOEs in the $^{13}$C-NOESY data) between the PTB domain and the FGFR peptides, for example.

To ensure mutant proteins are valid for functional analysis, it can be determined as to whether a mutation results in any significant perturbation of the overall conformation of the PTB domain, particularly the effects of mutation on the peptide binding sites. NMR spectroscopy is a powerful method for examining the effects of such a mutation on the conformation of the protein. One can readily obtain information about the global conformation of a mutant protein from the proton ($^1$H) 1D spectrum, by examining the chemical shift dispersion and peak line-width of NMR signals of amide, aromatic and aliphatic protons. Moreover, 2D $^1$H-$^{15}$N HSQC spectra reveal details of the effects of a mutation on both local and global conformation of the protein, since every single $^1$H/$^{15}$N signal (both the chemical shift and line-shape) in the NMR spectrum is a "reporter" for a particular amino acid residue. Thus, to assess how mutations effect protein stability and the overall protein conformation, the $^{15}$N HSQC spectra of mutated proteins can be compared to that of the wild-type protein.

Chemical-shift perturbations due to ligand binding have proven to be a reliable and sensitive probe for the ligand binding site of the protein. This is because the chemical-shift changes of the backbone amide groups are likely to reflect any changes in protein conformation and/or hydrogen bonding due to the peptide/ligand binding. To examine the effects of a mutation on the ligand binding (in this case the ligand is a peptide), peptide titration experiments can be conducted by following the changes of $^1$H/$^{15}$N signals of the mutant proteins as a function of the peptide concentration. These experiments indicate whether the peptide-binding site remains the same or changes in the mutants relative to the wild type protein. The effects of the mutation on the peptide binding affinity can also be examined by NMR spectroscopy. Due to the high binding affinity of the peptides for the wild type SNT-1 PTB domain, signals of the free and peptide-bound forms exhibit a slow exchange on the NMR time scale during the peptide titration. If the mutated proteins result in the reduction of the binding affinity, a change of the exchange phenomenon between the free and the ligand-bound signals should be observed in NMR spectrum. If the reduction in binding affinity causes the peptide binding to change from a slow exchange rate to a fast exchange rate, on the NMR time scale, then the peptide binding affinity can be determined from the NMR titration experiment. From these mutation analyses key amino acid residues that are important for binding either the tyrosine-phosphorylated TRKA receptor peptide or the non-phosphorylated FGF receptor peptide can be identified.

Protein Structure Determination by NMR Spectroscopy

The NMR results from the present invention are summarized in Table 1, which includes exemplary structural coordinates, Table 2, which contains the chemical shift data, Table 3, which contains the Hbond results, Table 4, which contains the unambiguous determinations, and Table 5, which contains the ambiguous determinations.

Backbone and Side-chain Assignments: Sequence-specific backbone assignment is achieved by using a suite of deuterium-decoupled triple-resonance 3D NMR experiments which include HNCA, HN(CO)CA, HN(CA)CB, HN(CO-CA)CB, HNCO, and HN(CA)CO experiments [Yamazaki, et al., *J. Am. Chem. Soc.* 116:11655-11666 (1994)]. The water flip-back scheme is used in these NMR pulse programs to minimize amide signal attenuation from water exchange. Sequential side-chain assignments are typically accomplished from a series of 3D NMR experiments with alternative approaches to confirm the assignments. These experiments include 3D $^{15}$N TOCSY—HSQC, HCCH-TOCSY, (H)C(CO)NH-TOCSY, and H(C)(CO)NH-TOCSY [see Clore and Gronenborn, *Meth. Enzymol.* 239:249-363 (1994); Sattler et al., *Prog. in Nuclear Magnetic Resonance Spec.* 4:93-158 (1999)].

Stereospecific Methyl Groups: Stereospecific assignments of methyl groups of Valine and Leucine residues are obtained from an analysis of carbon signal multiplet splitting using a fractionally $^{13}$C-labeled protein sample, which can be readily prepared using M9 minimal medium containing 10% $^{13}$C-/90% $^{12}$C-glucose mixture [see Neri, et al., *Biochemistry* 28:7510-7516 (1989)].

Dihedral Angle Restraints: Backbone dihedral angle ($\Phi$) constraints are generated from the $^3J_{HNH\alpha}$ coupling constants measured in a HNHA-J experiment [see Vuister, G. & Bax, A. *J. Am. Chem. Soc.* 115:7772-7777 (1993)]. Side-chain dihedral angles ($\chi_1$) can be obtained from short mixing time $^{15}$N-edited 3D TOCSY—HSQC [see Clore, et al., *J. Biomol. NMR* 1:13-22 (1991)] and 3D HNHB experiments [see Matson et al., *J. Biomol. NMR* 3:239-244 (1993)], which can also provide stereospecific assignments of β methylene protons.

Hydrogen Bonds Restraints: Amide protons that are involved in hydrogen bonds can be identified from an analysis of amide exchange rates measured from a series of 2D $^1$H/$^{15}$N HSQC spectra recorded after adding $^2$H$_2$O to the protein sample.

NOE Distance Restraints: Distance restraints are obtained from analysis of $^{15}$N, and $^{13}$C-edited 3D NOESY data, which can be collected with different mixing times to minimize spin diffusion problems. The nuclear Overhauser effect (NOE)-derived restraints are categorized as strong (1.8-3 Å), medium (1.8-4 Å) or weak (1.8-5 Å) based on the observed NOE intensities. A recently developed procedure for the iterative automated NOE analysis by using ARIA [see Nilges et al., *Prog. NMR Spectroscopy* 32:107-139 (1998)] can be employed which integrates with X-PLOR for structural calculations. To ensure the success of ARIA/X-PLOR-assisted NOE analysis and structure calculations, the ARIA assigned NOE peaks can be manually confirmed.

Intermolecular NOE Distance Restraints: For the structural determination of a protein/peptide complex, intermolecular NOE distance restraints can be obtained from a $^{13}$C-edited ($F_1$) and $^{15}$N, and $^{13}$C-filtered ($F_3$) 3D NOESY data set collected for a sample containing isotope-labeled protein and non-labeled peptide.

Structure Calculations and Refinements: Structures of the protein can be generated using a distance geometry/simulated annealing protocol with the X-PLOR program [see Nilges et al., *FEBS Lett.* 229:317-324 (1988); Kuszewski, et al., *J. Biolmol NMR* 2:33-56 (1992); Brunger, X-PLOR Version 3.1: A system for X-Ray crystallography and NMR (Yale University Press, New Haven, Conn., 1993)]. The structure calculations can employ inter-proton distance restraints obtained from $^{15}$N— and $^{13}$C-resolved NOESY spectra. The initial low-resolution structures can be used to facilitate NOE assignments, and help identify hydrogen bonding partners for slowly exchanging amide protons. The experimental restraints of dihedral angles and hydrogen bonds can be included in the distance restraints for structure refinements.

Protein-Structure Based Design of Agonists and Antagonists of The SNT/FGFR Complex Once the three-dimensional structure of the SNT/FGFR complex is determined, a potential drug or agent (antagonist or agonist) can be examined through the use of computer modeling using a docking program such as GRAM, DOCK, or AUTODOCK [Dunbrack et al., 1997, supra]. This procedure can include computer fitting of potential agents to the PTB domain of SNT-1, for example, to ascertain how well the shape and the chemical structure of the potential ligand will complement or interfere with the interaction between SNT-1 and FGFR [Bugg et al., *Scientific American*, December:92-98 (1993); West et al., *TIPS*, 16:67-74 (1995)]. Computer programs can also be employed to estimate the attraction, repulsion, and steric hindrance of the agent to the dimer-dimer binding site, for example. Generally the tighter the fit (e.g., the lower the steric hindrance, and/or the greater the attractive force) the more potent the potential drug will be since these properties are consistent with a tighter binding constant. Furthermore, the more specificity in the design of a potential drug the more likely that the drug will not interfere with related proteins. This will minimize potential side-effects due to unwanted interactions with other proteins.

Initially a potential drug could be obtained by screening a random peptide library produced by recombinant bacteriophage for example, [Scott and Smith, *Science*, 249:386-390 (1990); Cwirla et al., *Proc. Natl. Acad. Sci.*, 87:6378-6382 (1990); Devlin et al., *Science*, 249:404-406 (1990)] or a chemical library. An agent selected in this manner could be then be systematically modified by computer modeling programs until one or more promising potential drugs are identified. Such analysis has been shown to be effective in the development of HIV protease inhibitors [Lam et al., *Science* 263:380-384 (1994); Wlodawer et al., *Ann. Rev. Biochem.* 62:543-585. (1993); Appelt, *Perspectives in Drug Discovery and Design* 1:23-48 (1993); Erickson, *Perspectives in Drug Discovery and Design* 1:1-09-128 (1993)].

Such computer modeling allows the selection of a finite number of rational chemical modifications, as opposed to the countless number of essentially random chemical modifications that could be made, any of which any one might lead to a useful drug. Each chemical modification requires additional chemical steps, which while being reasonable for the synthesis of a finite number of compounds, quickly becomes overwhelming if all possible modifications needed to be synthesized. Thus through the use of the three-dimensional structural analysis disclosed herein and computer modeling, a large number of these compounds can be rapidly screened on the computer monitor screen, and a few likely candidates can be determined without the laborious synthesis of untold numbers of compounds.

Once a potential drug (agonist or antagonist) is Identified it can be either selected from a library of chemicals as are commercially available from most large chemical companies including Merck, GlaxoWelcome, Bristol Meyers Squib, Monsanto/Searle, Eli Lilly, Novartis and Pharmacia Upjohn, or alternatively the potential drug may be synthesized de novo. As mentioned above, the de novo synthesis of one or even a relatively small group of specific compounds is reasonable in the art of drug design.

The potential drug can then be tested in any standard binding assay (including in high throughput binding assays) for its ability to bind to SNT or fragment thereof comprising the PTB domain. Alternatively the potential drug can be tested for its ability to modulate (either inhibit or stimulate) a cellular signal that is dependent on the interaction of SNT with FGFR. When a suitable potential drug is identified, a second NMR structural analysis can optionally be performed on the binding complex formed between the SNT/FGFR complex and the potential drug. Computer programs that can be used to aid in solving such three-dimensional structures include QUANTA, CHARMM, INSIGHT, SYBYL, MACROMODE, and ICM, MOLMOL, RASMOL, AND GRASP [Kraulis, *J. Appl Crystallogr.* 24:946-950 (1991)]. Most if not all of these programs and others as well can be also obtained from the WorldWideWeb through the internet.

Using the approach described herein and equipped with the structural analysis disclosed herein, the three-dimensional structures of other SNT/receptor complexes can more readily be obtained and analyzed. Such analysis will, in turn, allow corresponding drug screening methodology to be performed using the three-dimensional structures of such related complexes.

For all of the drug screening assays described herein further refinements to the structure of the drug will generally be necessary and can be made by the successive iterations of any and/or all of the steps provided by the particular drug screening assay, including further structural analysis by NMR, for example.

Phage Libraries for Drug Screening.

Phage libraries have been constructed which when infected into host *E. coli* produce random peptide sequences of approximately 10 to 15 amino acids [Parmley and Smith, Gene 73:305-318 (1988), Scott and Smith, Science 249:386-249 (1990)]. Specifically, the phage library can be mixed in low dilutions with permissive *E. coli* in low melting point LB agar which is then poured on top of LB agar plates. After incubating the plates at 37° C. for a period of time, small clear plaques in a lawn of *E. coli* will form which represents active phage growth and lysis of the *E. coli*. A representative of these phages can be absorbed to nylon filters by placing dry filters onto the agar plates. The filters can be marked for orientation, removed, and placed in washing solutions to block any remaining absorbent sites. The filters can then be placed in a solution containing, for example, a radioactive PTB domain (e.g., the peptide comprising amino acid residues 11-140 of SEQ ID NO:1). After a specified incubation period, the filters can be thoroughly washed and developed for autoradiography. Plaques containing the phage that bind to the radioactive PTB domain can then be identified. These phages can be further cloned and then retested for their ability to bind to the PTB domain as before. Once the phage has been purified, the binding sequence contained within the phage can be determined by standard DNA sequencing techniques. Once the DNA sequence is known, synthetic peptides can be generated which are encoded by these sequences.

These peptides can be tested, for example, for their ability to e.g., interfere with the binding of SNT with FGFR.

The effective peptide(s) can be synthesized in large quantities for use in in vivo models and eventually in humans to treat certain tumors. It should be emphasized that synthetic peptide production is relatively non-labor intensive, easily manufactured, quality controlled and thus, large quantities of the desired product can be produced quite cheaply. Similar combinations of mass produced synthetic peptides have recently been used with great success [Patarroyo, *Vaccine*, 10:175-178 (1990)].

Drug Screening Assays

The drug screening assays of the present invention may use any of a number of means for determining the interaction between an agent or drug and SNT and/or FGFR. In one such assay, a drug can be specifically designed to bind to the PTB domain of SNT-1 through NMR based methodology. [Shuker et al., *Science* 274:1531-1534 (1996) hereby incorporated by reference in its entirety.] In a particular embodiment, analogs of the FGFR derived peptide having the amino acid sequence of SEQ ID NO:3 are used. In a particular embodiment of this type, the peptide has the amino acid sequence of SEQ ID NO:4. In another such embodiment of this type, the peptide has the amino acid sequence of SEQ ID NO:5. Alternatively, a library of low molecular weight compounds can be screened to identify a binding partner for the PTB domain. Any such chemical library can be used including those discussed above.

The assay: begins with contacting a compound with a $^{15}$N-labeled SNT PTB domain. Binding of the compound with the SNT PTB domain can be determined by monitoring the $^{15}$N— or $^{1}$H-amide chemical shift changes in two dimensional $^{15}$N-heteronuclear single-quantum correlation ($^{15}$N—HSQC) spectra upon the addition of the compound to the $^{15}$N-labeled SNT PTB domain. Since these spectra can be rapidly obtained, it is feasible to screen a large number of compounds [Shuker et al., *Science* 274:1531-1534 (1996)]. A compound is identified as a potential ligand if it binds to the SNT PTB domain. In a further embodiment, the potential ligand can then be used as a model structure, and analogs to the compound can be obtained (e.g., from the vast chemical libraries commercially available, or alternatively through de novo synthesis). The analogs are then screened for their ability to bind the SNT PTB domain to obtain a ligand. An analog of the potential ligand is chosen as a ligand when it binds to the SNT PTB domain with a higher binding affinity than the potential ligand. In a preferred embodiment of this type the analogs are screened by monitoring the $^{15}$N— or $^{1}$H-amide chemical shift changes in two dimensional $^{15}$N-heteronuclear single-quantum correlation ($^{15}$N—HSQC) spectra upon the addition of the analog to the $^{15}$N-labeled SNT domain as described above.

In another further embodiment, compounds are screened for binding to two nearby sites on an SNT PTB domain. In this case, a compound that binds a first site of the SNT PTB domain does not bind a second nearby site. Binding to the second site can be determined by monitoring changes in a different set of amide chemical shifts in either the original screen or a second screen conducted in the presence of a ligand (or potential ligand) for the first site. From an analysis of the chemical shift changes the approximate location of a potential ligand for the second site is identified. Optimization of the second ligand for binding to the site is then carried out by screening structurally related compounds (e.g., analogs as described above). When ligands for the first site and the second site are identified, their location and orientation in the ternary complex can be determined experimentally either by NMR spectroscopy or X-ray crystallography. On the basis of this structural information, a linked compound is synthesized in which the ligand for the first site and the ligand for the second site are linked. In a preferred embodiment of this type the two ligands are covalently linked. This linked compound is tested to determine if it has a higher binding affinity for the SNT PTB domain than either of the two indiviual ligands. A linked compound is selected as a ligand when it has a higher binding affinity for the SNT PTB domain than either of the two ligands. In a preferred embodiment the affinity of the linked compound with the SNT PTB domain is determined monitoring the $^{15}N$— or $^1H$-amide chemical shift changes in two dimensional $^{15}N$-heteronuclear single-quantum correlation ($^{15}N$—HSQC) spectra upon the addition of the linked compound to the $^{15}N$-labeled SNT PTB domain as described above.

A larger linked compound can be constructed in an analogous manner, e.g., linking three ligands which bind to three nearby sites on the SNT PTB domain to form a multilinked compound that has an even higher affinity for the SNT PTB domain than linked compound.

In another assay, a SNT PTB domain is placed on or coated onto a solid support. Methods for placing the peptides or proteins on the solid support are well known in the art and include such things as linking biotin to the protein and linking avidin to the solid support. An agent is allowed to equilibrate with the SNT PTB domain to test for binding. Generally, the solid support is washed and agents that are retained are selected as potential drugs. In a particular embodiment of this type, the SNT PTB domain comprises amino acid residues 11-140 of SEQ ID NO:1.

The agent may be labeled. For example, in one embodiment radiolabeled agents are used to measure the binding of the agent. In another embodiment the agents have fluorescent markers. In yet another embodiment, a Biocore chip (Pharmacia) coated with the SNT PTB domain is used and the change in surface conductivity can be measured.

In yet another embodiment, the affect of a prospective drug (a test compound or agent) on a SNT PTB domain is assayed in a living cell that contains or can be induced to contain SNT-1 and FGFR. The cell can also contain or can be constructed to contain one or more reporter genes, such as a heterologous gene comprising a nucleic acid encoding luciferase, green fluorescent protein, chloramphenicol acetyl transferase, and/or β-galactosidase etc. Such reporter genes can be operably linked to a promoter comprising a binding site for a transcription factor under the control of the SNT/FGFR dependent cellular signaling pathway. Cells that naturally encode a FGFR and SNT-1 may be used, or alternatively a cell that is transfected with plasmids encoding the reporter proteins can be used, though care must be taken to ensure that the requisite participants in the SNT/FGFR dependent cellular signaling pathway are also present.

Assays for detecting the reporter genes products are readily available in the literature. For example, luciferase assays can be performed according to the manufacturer's protocol (Promega), and β-galactosidase assays can be performed as described by Ausubel et al. [in *Current Protocols in Molecular Biology*, J. Wiley & Sons, Inc. (1994)]. The preparation of such plasmid containing reporter genes is now routine in the art, and many appropriate plasmids are now commercially available which can be readily modified for such assays.

The prospective drug is generally tested under conditions in which the FGFR has been activated. The FGF receptor can be activated by an antibody or preferably FGF. Alternatively, a permantively activated FGF can be constitutively expressed. In one embodiment, the expression of SNT-1 is constitutive. The amount (and/or activity) of reporter protein produced in the absence and presence of prospective drug can then be determined and compared. Prospective drugs which reduce the amount (and/or activity) of the reporter protein produced are candidate antagonists of the SNT/FGFR complex, whereas prospective drugs which increase the amount (and/or activity) of reporter protein produced are candidate agonists.

Labels

Suitable labels include enzymes, fluorophores (e.g., fluorescein isothiocyanate (FITC), phycoerythrin (PE), Texas red (TR), rhodamine, free or chelated lanthanide series salts, especially $Eu^{3+}$; to name a few fluorophores), chromophores, radioisotopes, chelating agents, dyes, colloidal gold, latex particles, ligands (e.g., biotin), and chemiluminescent agents. When a control marker is employed, the same or different labels may be used for the test and control marker gene.

In the instance where a radioactive label, such as the isotopes $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g, ultraviolet light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932 and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology,* 70:419-439 (1980) and in U.S. Pat. No. 4,857, 453.

Suitable enzymes include, but are not limited to, alkaline phosphatase, β-galactosidase, green fluorescent protein and its derivatives, luciferase, and horseradish peroxidase.

Other labels for use in the invention include magnetic beads or magnetic resonance imaging labels.

Antibodies to the SNT and FGFR Fragments

According to the present invention, the SNT and FGFR peptides and fragments as produced by a recombinant source, or through chemical synthesis, or through the modification of these peptides and fragments; and derivatives or analogs thereof, including fusion proteins, may be used as an immunogen to generate antibodies that specifically interfere with the formation of the SNT/FGFR complex. Such antibodies include but are not limited to polyclonal, monoclonal, chimeric, single chain, Fab fragments, and a Fab expression library.

Various procedures known in the art may be used for the production of the polyclonal antibodies. For the production of antibody, various host animals can be immunized by injection with the peptide having the amino acid sequence of SEQ ID NO:3 for example, or a derivative (e.g., a fusion protein) thereof, including but not limited to rabbits, mice, rats, sheep, goats, etc. In one embodiment, the peptide can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (*bacille Calmette-Guerin*) and *Corynebacterium parvum*.

For preparation of monoclonal antibodies directed toward the peptides or protein fragments of the present invention, or analog, or derivative thereof, any technique that provides for the production of antibody molecules by continuous cell lines in culture may be used. These include but are not limited to the hybridoma technique originally developed by Kohler and Milstein [*Nature,* 256:495-497 (1975)], as well as the trioma technique, the human B-cell hybridoma technique [Kozbor et al., *Immunology Today,* 4:12 (1983); Cote et al., *Proc. Natl. Acad. Sci. U.S.A.,* 80:2026-2030 (1983)], and the EBV-hybridoma technique to produce human monoclonal antibodies [Cole et al., in *Monoclonal Antibodies and Cancer Therapy,* Alan R. Liss, Inc., pp. 77-96 (1985)]. In an additional embodiment of the invention, monoclonal antibodies can be produced in germ-free animals utilizing recent technology [PCT/US90/02545]. In fact, according to the invention, techniques developed for the production of "chimeric antibodies" [Morrison et al., *J. Bacteriol.,* 159:870 (1984); Neuberger et al., *Nature,* 312:604-608 (1984); Takeda et al., *Nature,* 314:452-454 (1985)] by splicing the genes from a mouse antibody molecule specific for the peptide having the amino acid sequence of SEQ ID NO:3 together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies [U.S. Pat. Nos. 5,476, 786 and 5,132,405 to Huston; U.S. Pat. No. 4,946,778] can be adapted to produce specific single chain antibodies. An additional embodiment of the invention utilizes the techniques described for the construction of Fab expression libraries [Huse et al., *Science,* 246:1275-1281 (1989)] to allow rapid and easy identification of monoclonal Fab fragments with the desired specificity.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immununodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of an FGFR, for example, one may assay generated hybridomas for a product which binds to an FGFR fragment containing such epitope and choose those which do not cross-react with FGFR fragments that do not include that epitope.

In a specific embodiment, antibodies that interfere with the formation of the SNT/FGFR complex can be generated. Such antibodies can be tested using the assays described could potentially be used in anti-tumor therapies.

The present invention may be better understood by reference to the following non-limiting Example, which is provided as exemplary of the invention. The following example is presented in order to more fully illustrate the preferred embodiments of the invention. It should in no way be construed, however, as limiting the broad scope of the invention.

EXAMPLE

The Three-Dimensional Structure of the SNT-1 PTB Domain With the FGF Receptor

Introduction

Phosphotyrosine binding (PTB) domains represent a group of structurally related but functionally divergent protein modules that play an important role in regulating protein-phosphotyrosine, protein-phospholipids, or protein-protein interactions [Pawson, and Scott, *Nature* 278: 2075-2080 (1997); Zhou and Fesik, *Prog. Biophys. Molec. Biol.* 64:221-235 (1995)]. The amino-terminal PTB domains of the newly discovered lipid-anchored docking proteins SNT-1 and SNT-2 have been shown to possess a unique ability to recognize both a canonical NPXpY motif on the activated nerve growth factor (NGF) receptor, and a tyrosine and asparagine-free motif on the fibroblast growth factor (FGF) receptor [Xu et al., *J. Biol. Chem.* 273:17987-17990 (1998); Kouhara et al. *Cell* 89:693-702 (1997); Meakin et al., *J. Biol. Chem.* 274: 9861-9870 (1999)].

Materials and Methods

Sample Preparation: A cDNA fragment encoding the SNT-1 PTB domain was cloned into a modified pET28b vector (Novagen) that produced the recombinant protein with a cleavable hexa-histidine (His$_6$) tag at the C-terminus. Uniformly $^{15}$N— and $^{15}$N/$^{13}$C-labeled proteins were prepared by growing *Escherichia coli* BL21(DE3) cells in a minimal medium containing $^{15}$NH$_4$Cl with or without $^{13}$C$_6$-glucose. A uniformly $^{15}$N/$^{13}$C-labeled and fractionally deuterated protein was prepared using medium with 75% $^2$H$_2$O. The protein was over-expressed largely in soluble form and purified by affinity chromatography on a nickel-IDA column (Invitrogen) followed by cleavage of the His$_6$ tag upon thrombin treatment. The cleaved protein contains an additional LVPR sequence at the C-terminus from the engineered thrombin site. The protein was unstable in its free form and quickly aggregated or became partially unfolded at room temperature. To ensure structural integrity, the protein was further subjected to a protein refolding procedure followed by ion-exchange chromatography. Synthetic peptides were prepared on a MilliGen 9050 peptide synthesizer (Perkin Elmer) using Fmoc/HBTU chemistry. NMR samples contained the SNT-1 PTB domain/hFGFR1 peptide complex (1:1) of 0.5 mM in 100 mM phosphate buffer of pH 6.5, 5 mM DTT-d$_{10}$ and 0.5 mM EDTA in H$_2$O/$^2$H$_2$O (9/1) or $^2$H$_2$O.

NMR Spectroscopy: NMR spectra were acquired at 30° C. on a Bruker DRX600 or DRX500 spectrometer. The backbone and side-chain $^1$H, $^{13}$C and $^{15}$N resonances of the protein were assigned using deuterium-decoupled triple-resonance experiments of HNCA, HN(CO)CA, HNCACB, HN(CO)CACB and (H)C(CO)NH-TOCSY [Yamazaki, et al., *J. Am. Chem. Soc.* 116:11655-11666 (1994); Sattler et al., *Prog. in Nuclear Magnetic Resonance Spec.* 4:93-158 (1999)] recorded using uniformly $^{15}$N/$^{13}$C-labeled and fractionally deuterated protein in complex with a non-isotopically labeled hFGFR1 peptide. The side-chain assignments were completed using 3D HCCH-TOCSY [Clore, and Gronenbom, *Meth. Enzymol.* 239:249-363 (1.994)] data collected from a uniformly $^{15}$N/$^{13}$C-labeled protein/non-labeled peptide complex NOE-derived distance restraints were obtained from $^{15}$N— or $^{13}$C-edited 3D NOESY spectra [Clore, and Gronenborn, *Meth. Enzymol.* 239:249-363 (1994)]. φ-angle restraints were determined from $^3J_{HN,H\alpha}$ coupling constants measured in a 3D HNHA-J spectrum [Clore, and Gronenborn, *Meth. Enzymol.* 239:249-363 (1994)]. Slowly exchanging amide protons were identified from a series of 2D $^{15}$N—HSQC spectra recorded after the H$_2$O buffer was changed to $^{2H}_2$O buffer. The peptide resonances were assigned using $^{13}$C/$^{15}$N-filtered 2D NOESY and TOCSY spectra [Sattler et al., *Prog. in Nuclear Magnetic Resonance Spec.* 4:93-158 (1999)] collected from a $^{15}$N/$^{13}$C-labeled protein/non-labeled peptide complex. The intermolecular NOEs used in defining the structure of the SNT-1 PTB domain/hFGFR1 complex were detected in $^{13}$C— or $^{15}$N-edited (F$_1$), $^{13}$C/$^{15}$N-filtered (F$_3$) 3D NOESY spectra. All NMR spectra were processed with NMRPipe/NMRDraw [Delaglio et al., *J. Biomol. NMR* 6:277-293 (1995)] and analyzed using NMRView [Johnson and Blevins *J. Biomol. NMR* 4:603-614 (1994)]. Chemical shift assignments of the SNT PTB domain and the hFGFR1 peptide have been deposited in the BioMagResBank (BMRB) under accession number 4790.

Structure Calculations: Structures of the SNT-1 PTB domain in complex with the hFGFR1 peptide were calculated with a distance geometry and simulated annealing protocol using the X-PLOR program [Brunger, X-PLOR Version 3.1: A system for X-Ray crystallography and NMR (Yale University Press, New Haven, Conn., 1993)]. NOE distance and dihedral angle restraints were treated with a square-well potential of 50 kcal mol$^{-1}$ Å$^{-2}$. A total of 2448 manually assigned NOE-derived distance restraints were obtained from the $^{15}$N— or $^{13}$C-edited NOESY data, including 251 intra-peptide and 258 intermolecular distance restraints. Additionally, 255 unambiguous and 52 ambiguous distance restraints were identified from the NOE data by using ARIA [Nilges and O'Donoghue, *Prog. NMR Spectroscopy* 32:107-139 (1998)]. The final structure calculations employed a total of 2755 NOE restraints obtained from the manual and the ARIA-assisted assignments, 2703 of which were unambiguously assigned NOE-derived distance restraints that comprise of 1072 intra-residue, 466 sequential, 216 medium-range and 949 long-range NOEs. In addition, 70 hydrogen-bond distance restraints for 35 hydrogen bonds and 19 (φ-angle restraints were also used in the structure calculations. For the ensemble of the final 20 structures, no distance or torsional angle restraint was violated by more than 0.4 Å or 5°, respectively. The total, distance violation and dihedral violation energies were 262.0±6.0 kcal mol$^{-1}$, 74.4±1.7 kcal mol$^{-1}$ and 0.82±0.08 kcal mol$^{-1}$, respectively. The Lennard-Jones potential, which was not used during any refinement stage, was −659.3±23.1 kcal mol$^{-1}$ for the final structures. Ramachandran plot analysis by Procheck-NMR [Laskowski et al., *J. Biomol. NMR* 8:477-486 (1996)] showed that in the final structures of the complex, 98.1 % of the backbone geometries of the non-Gly and non-Pro residues in the complex (protein residues 18-116 and peptide residues 412-430), and nearly 100% in the secondary structure (protein residues 19-24, 35-40, 45-49, 52-57, 63-68, 71-76, 85-90, 94-107 and 111-115; and peptide residues 426-430) lie within energetically favorable or allowed regions.

Mutagenesis and Yeast Two-Hybrid Binding Assays: The yeast two-hybrid binding studies of the SNT-1 PTB domain binding to hFGFR1 or tyrosine-phosphorylated TRK were performed as described previously [Xu et al., *J. Biol. Chem.* 273:17987-17990 (1998)]. Briefly, SNT-1 cDNA fragments were cloned into the pACT2 expression vector (Clontech) for expression as GAL4 DNA activation domain (AD) fusion proteins followed by C-terminal AU1-epitope tags. The juxtamembrane region of hFGFR1 was cloned into the pAS2-1 expression vector (Clontech) for expression as a GAL4 DNA binding domain (BD) fusion protein. This plasmid served as a template for site-directed mutagenesis of hFGFR1 using the QuikChange kit (Stratagene). DNA sequencing confirmed the mutations. AD and BD plasmids were co-transformed into *Saccharomyces cerevisiae* strain pJ69-4A and plated onto selective media. The synthetic medium lacking the amino acids Leu and Trp (Leu$^-$, Trp$^-$) selected for plasmid uptake. Medium lacking His, Leu and Trp (His$^-$, Leu$^-$, Trp$^-$) but containing 3 mM 3-aminotriazole was used to select for interaction of the AD and BD fusion proteins. Levels of protein interaction were scored by relative colony growth on these plates. Expression of the SNT-1 protein was confirmed by immunoprecipitation from yeast lysates using an anti-AU1 monoclonal antibody (BAbCo). Western blotting was performed using an anti-AD antibody (Santa Cruz Biotech), goat anti-mouse IgG conjugated with horseradish-peroxidase, and developed by chemiluminescence. Similarly, expression of wild type and mutant hFGFR1 was detected by immunoprecipitation with a rabbit polyclonal antibody specific for BD (Santa Cruz Biotech) and western blotting with mouse monoclonal anti-BD antibody (Santa Cruz Biotech).

Ligand titration. Ligand titration experiments were performed by recording a series of 2D $^{15}$N— and $^{13}$C-HSQC spectra on the uniformly $^{15}$N—, and $^{15}$N/$^{13}$C-labeled SNT-1 PTB domain (~0.3 mM), respectively, in the presence of different amounts of the peptide ligands concentration ranging from 0 to ~2.0 mM. The protein sample and the stock solutions of the ligands were all prepared in the same aqueous buffer containing 100 mM phosphate and 5 mM perdeuterated DTT at pH 6.5.

Summary

In an effort to understand the detailed molecular mechanisms by which SNTs regulate FGF and NGF receptor signaling, the three-dimensional structure of the SNT-1 PTB domain in complex with a peptide derived from the known SNT-1 binding site on the FGF receptor has been determined using NMR spectroscopy. On the basis of the new structural information, key amino acid residues are disclosed that are important for the SNT-1 PTB domain interactions with the TRKA and FGF receptors.

Figure 3A:
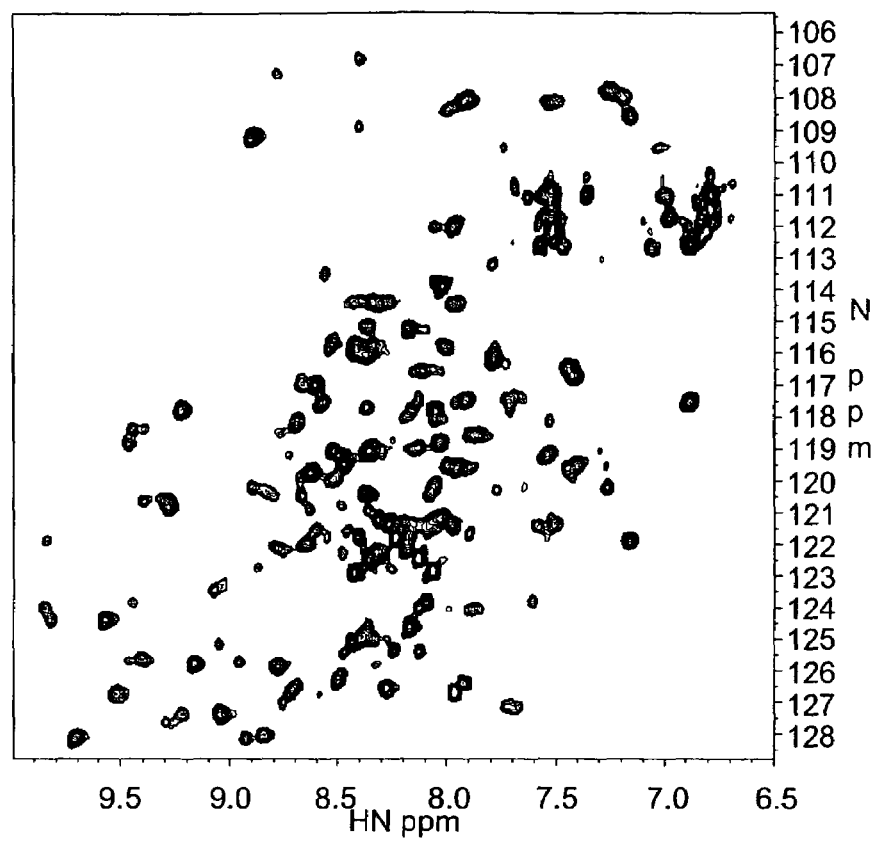
FIG. 3A depicts the 2D $^1H/^{15}N$-HSQC spectrum of the SNT-1 PTB domain (0.25 mM) complexed to a FGFR peptide (1:1). The spectrum was recorded on a Bruker DRX 500 MHz NMR spectrometer for the protein in 50 mM phosphate buffer of pH 6.5 containing 5 mM DTT and 0.5 mM EDTA at 25° C.
Figure 3B:
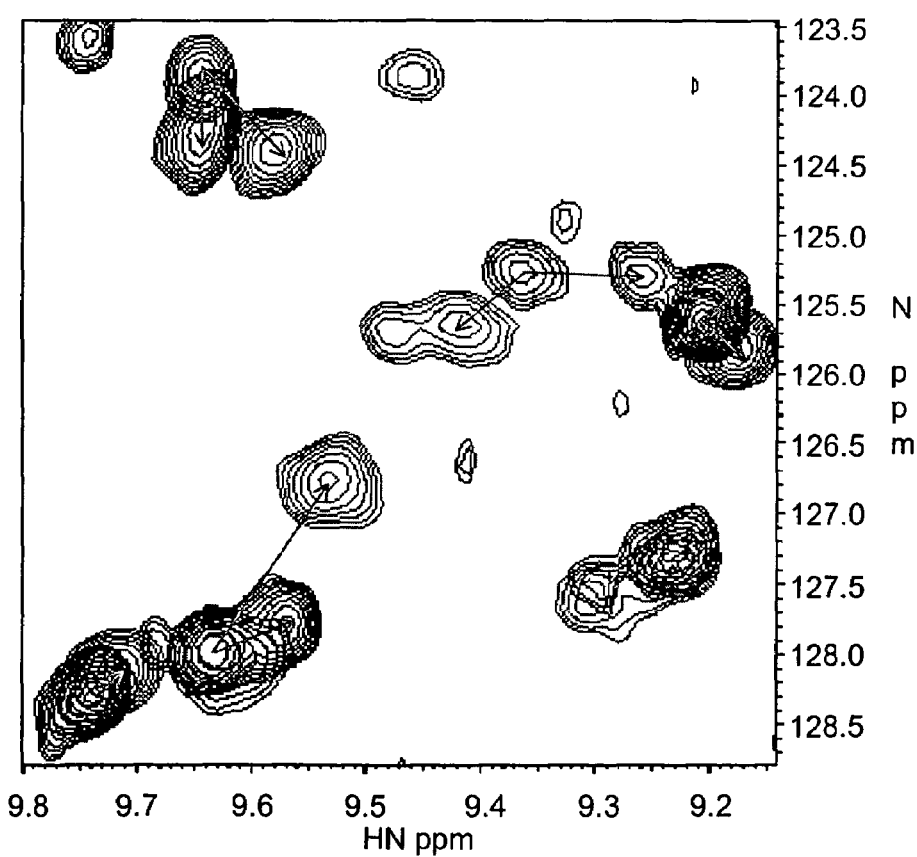
FIG. 3B depicts the effects of a FGFR peptide or a TRKA phosphopeptide binding on the backbone amide signals in the HSQC spectrum of the SNT-1 PTB domain. The amide peaks of the protein in the free, the FGFR peptide-, or the TRKA phosphopeptide-complexed forms are color-coded in black, red, and blue, respectively. Green arrows indicate the shifts of the amide signals upon binding to the corresponding peptides.

To examine the SNT-1 PTB domain binding to the peptides derived from tyrosine-phosphorylated TRKA and non-phosphorylated FGF receptors, the receptor peptides were titrated into the protein solution and the chemical shift perturbations of the protein backbone amide resonances in the HSQC spectra were monitored. The salient inferences emerged from the NMR titration data are that the FGF and: TRKA receptor peptides bind to the PTB domain in specific but distinct manners. This conclusion is supported by the observation that distinct sets of amino acid residues undergo chemical shift perturbation upon binding to the different peptides in the NMR titration (FIG. 3B). In addition, binding to the FGFR peptide results in more residues to undergo chemical shift changes than the TRKA binding. Taken together, these results clearly indicate that the SNT-1 PTB domain employs two different mechanisms in its interactions with the FGF and TRKA receptor peptides.

The human suc-1-associated neurotrophic (SNT) factor target, GenBank Accession No. 5730057, has the amino acid sequence of SEQ ID NO:1. The mouse (Mus musculus) fibroblast growth factor receptor-1, GenBank Accession No. AAC52182, has the amino acid sequence of SEQ ID NO:2. The protein fragments employed in the NMR structural determination (summarized in Tables 1-5) were the PTB Domain of SNT-1 comprising amino acid residues 11-140 of SEQ ID NO:1 and a small fragment of FGFR1 comprising amino acid residues 409-430 of SEQ ID NO:2, [HSQMA VHKLA KSIPL RRQVT VS (SEQ ID NO:3)]. The NMR spectra were carried out at a concentration of 0.5 mM SNT-1/FGFR1 in a 1:1 complex in a 0.1 M sodium phosphate buffer pH 6.5 containing 5 mM DTT and 1 mM EDTA. The results of the NMR analysis are included below in Tables 1-5. The depiction of the structure is shown in FIG. 2.

Through the use of the information disclosed herein chemical compounds that can inhibit or block the SNT-1 PTB domain interaction with FGF receptor or the NGF TRKA receptor have been designed and examined. One such compound is a tyrosine-phosphorylated peptide having the amino acid sequence of LVIAGNPApYRS, SEQ ID NO:4 (where pY stands for phosphotyrosine). This peptide can bind to the SNT-1 PTB domain with high affinity of $K_d$~1 μM. The affinity of the SNT-1 PTB domain binding for this peptide is about 10-fold higher than that for the FGFR derived peptide having the amino acid sequence of SEQ ID NO:3. Furthermore, this peptide partially overlaps with the binding of the FGFR peptide having the amino acid sequence of SEQ ID NO:3 on the SNT-1 PTB domain. These results suggest that this tyrosine-phosphorylated peptide could act as a competitive inhibitor to block the interaction between the SNT-1 PTB domain and FGFR, and thus could serve as basis for further development of small molecule mimetics that inhibit this interaction in cells.

The present study has also identified several key amino acid residues in both the SNT-1 PTB domain and FGFR1 that are important for the SNT-1 PTB domain interactions with the FGF receptor or the NGF TRKA receptor. The following amino acid residues were identified in the SNT-1 PTB domain of SNT-1 (having the amino acid sequence of SEQ ID NO:1): Asp 28, Asp 29 Phe 89, Val 112, Glu 114, and Glu 119

In the SNT-1 PTB binding domain of FGFR1 of the FGF receptor having the amino acid sequence of SEQ ID NO:2 the following amino acid residues were identified: Val 414, Leu 417, Ile 421, Leu 423, Arg 425, Val 427, and Val 429.

Results

Structure of the SNT PTB Domain: Nuclear magnetic resonance (NMR) studies were conducted using a 1:1 complex of SNT-1 PTB domain (residues 11-140 of SEQ ID NO:1.) and a 22-residue peptide derived from the juxtamembrane region of hFGFR1 (residues 409-430 of SEQ ID NO:2) (FIGS. 1A and 1B). The dissociation constant ($K_D$) of the protein/peptide complex was estimated to be ~10 μM using the isothermal titration calorimetry (ITC) technique. This result is consistent with the interaction being in slow to intermediate exchange on the NMR timescale in NMR titration experiments. The well-defined structure of this complex was determined from a total of 2844 NMR-derived restraints (FIG. 2A). The protein structure consists of a β-sandwich containing two nearly orthogonal, antiparallel β-sheets capped at one end by an amphipathic α-helix (FIGS. 2B and 2C), as anticipated from a classical PTB domain. The SNT-1 structure, however, possesses several unforeseen features that are unique for the conserved PTB domain scaffold. First, unlike all other known PTB domain structures that end with a C-terminal α-helix [Forman-Kay and Pawson, Curr. Opin. Struct. Biol. 9:690-695 (1999)], the SNT-1 PTB domain has an additional β-strand (β8) extending from its C-terminal α-helix (α1) that molds the hFGFR1 peptide into the second antiparallel β-sheet (see below). Second, boundaries of secondary structure elements between SNT and IRS PTB domains do not necessarily coincide with their amino acid conservation, such as the conserved VEE motif of β8 (residues 113-115), suggesting that tertiary interactions are very important in defining structure elements. Third, a C-terminal portion of the SNT-1 construct (residues 116-136) (FIG. 1A), which is highly homologous (~45% identity) to al in the IRS-1 PTB domain, is largely structurally disordered. The loss of helical conformation is perhaps due to the presence of Pro residues and change of amphipathic nature of the sequence, which could disrupt helical propensity and alter interactions with other parts of the protein, respectively. While reasons for the conformational discrepancy between these homologous sequences are evident from structural analysis, the functional implications of their evolutionary relationship are not clear. Finally, the sequence comprising residues 94-107 in SNT-1, predicted to be a large insert from sequence homology alignment with IRS proteins, actually forms an α-helix (α1) that blocks one side of the β-sandwich. Together, these unique structural features of the SNT-1 PTB domain may confer its distinct function.

Figure 2B:
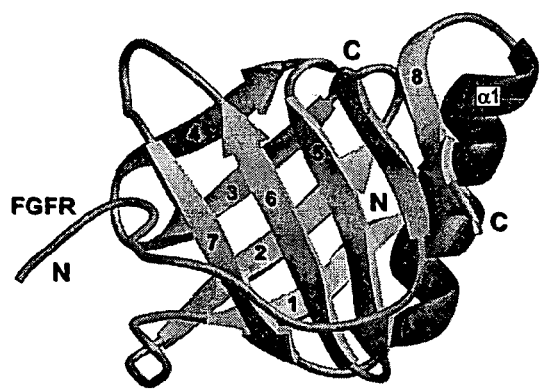
Figure 2C:
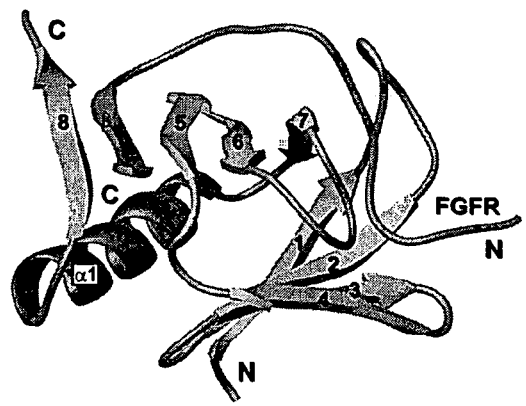
Figure 2D:
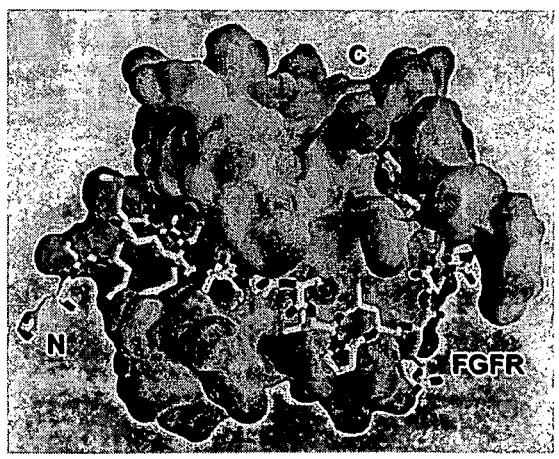
Figure 4A:
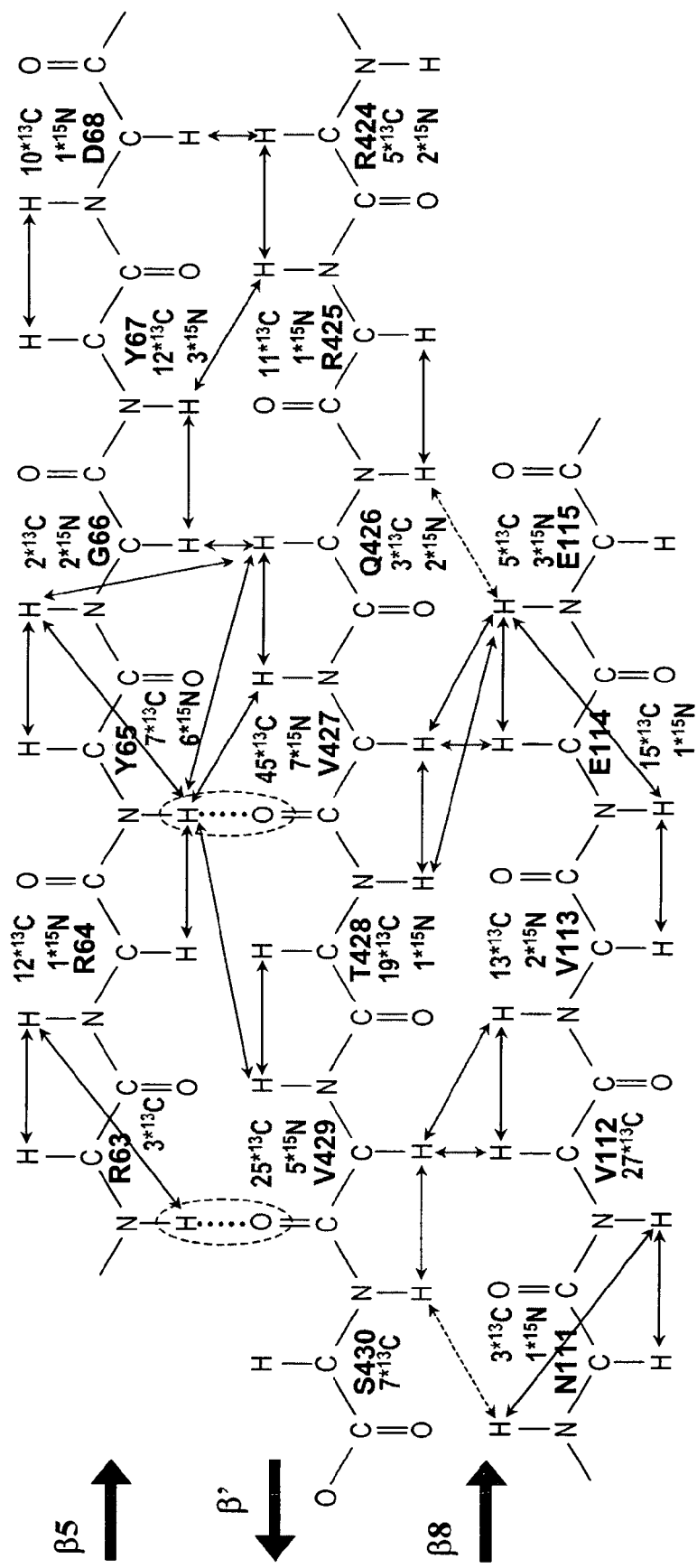
FIGS. 4A-4E depict the intermolecular interactions in the SNT-1 PTB domain/hFGFR1 complex.
Figure 4C:
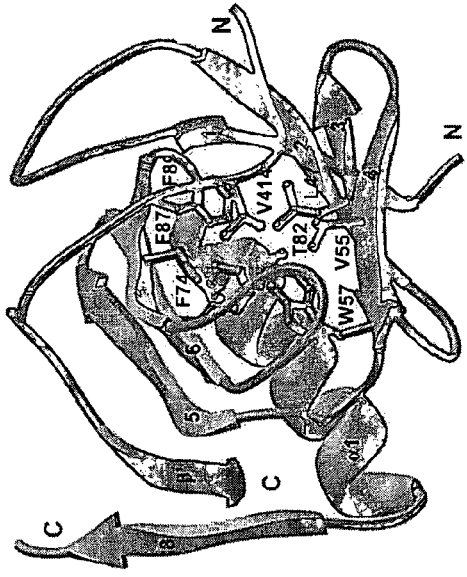
Figure 4E:
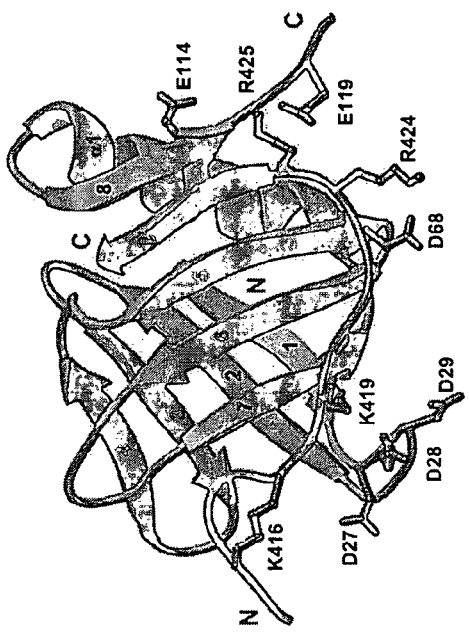
Figure 4B:
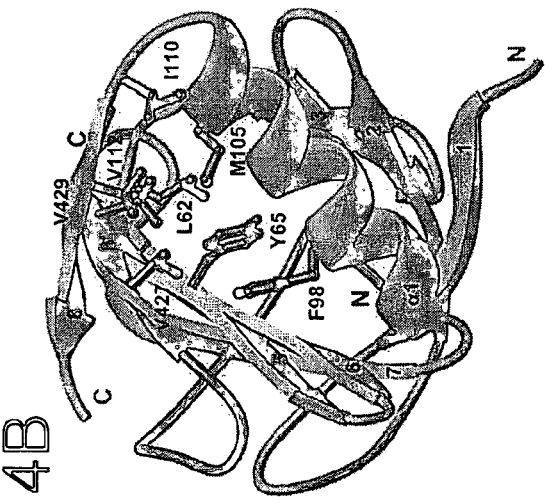
Figure 4D:
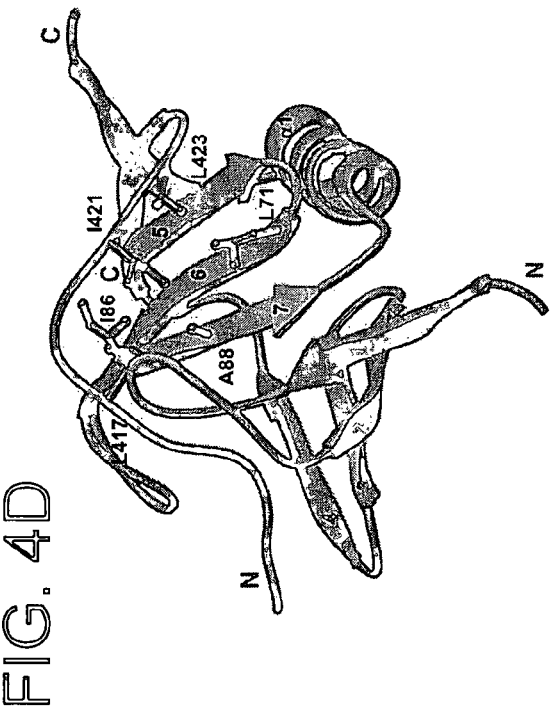

Interactions between hFGFR1 Peptide and the SNTPTB Domain: The hFGFR1 peptide wraps around the protein molecule with an unusual backbone conformation containing two nearly 90° turns that are oriented orthogonal to each other (FIGS. 2B and 2C). The peptide interacts extensively with the protein by clasping both sides of the β-sandwich (FIG. 2D). The estimated surface area of SNT-1 buried by the bound peptide is ~2025 Å$^2$, with 18 of the 22 peptide residues displaying intermolecular NOEs to many protein residues (FIG. 1B). The C-terminal QVTVS segment of the peptide (residues 426-430) adopts an antiparallel β-strand (β') sandwiched between β5 and β8. Two intermolecular hydrogen bonds bridging β' and β5, and a large number of NOEs characteristic of the antiparallel β-sheet are observed between backbone atoms of the complex (FIG. 4A). Side-chains of Val-427 and Val-429 interact extensively with Leu-62, Tyr-65, Phe-98, Met-105, Ile-110 and Val-112 in a hydrophobic core formed between β5 and α1 (FIG. 4B). The peptide fastens onto the other side of the β-sandwich by embedding its N-terminal MAVH segment (residues 412-415) into a large hydrophobic cavity bounded by the three loops connecting β1/β2, β3/β4 and β16/β7. In particular, methyl groups of Val-414 are completely immersed in an aromatic pool of Trp-57, Phe-74, Phe-87 and Phe-89, and also contact Leu-47, Vat-55 and Thr-82 (FIG. 4C). Moreover, Leu-417, Ile-421 and Leu-423 located in the center of the peptide bind to otherwise solvent-exposed hydrophobic residues Leu-71, Ile-86 and Ala-88 on the surface of the second β-sheet (FIG. 4D). In addition to hydrophobic interactions, complementary electrostatic interactions are observed, largely localized at the two turns in the peptide. At one turn, Arg-424 pairs with Asp-68, while Arg-425 interacts with Glu-114 and Glu-119. At the other turn, Lys-416 and Lys-419 show interactions with a contiguous patch of three solvent-accessible residues Asp-27, Asp-28 and Asp-29 (FIG. 4E). These results indicate that both hydrophobic and electrostatic interactions are important for SNT-1 and hFGFR1 recognition.

Figure 6A:
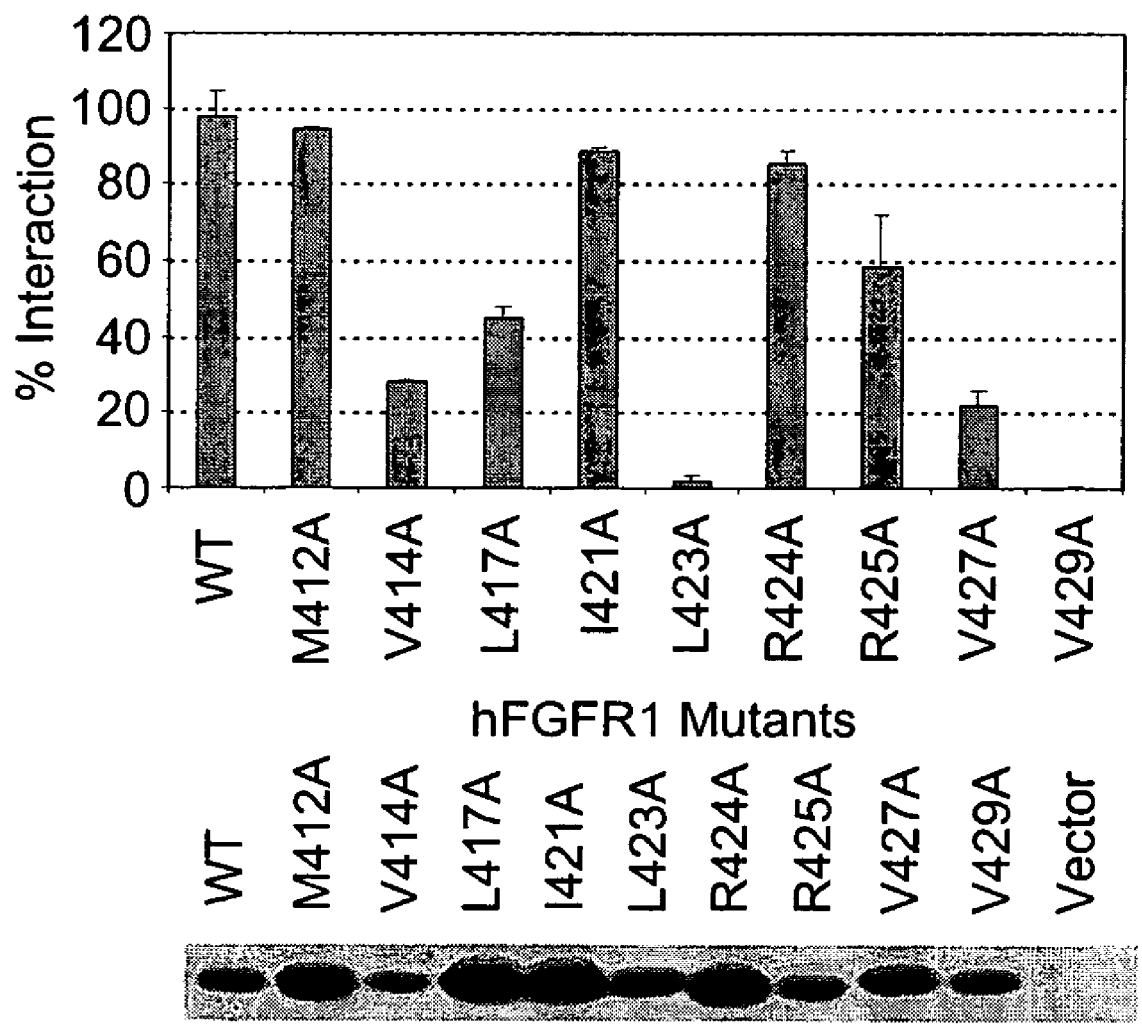
FIGS. 6A-6D show the mutational analysis of the SNT-1 PTB domain interactions with FGFRs or TRKs.

To determine the relative contributions of specific hFGFR1 residues to SNT-1 recognition, site-directed mutagenesis was used to alter the peptide residues that show intermolecular NOEs to the protein (FIG. 1B). The resulting hFGFR1 mutants were analyzed for SNT-1 interaction by yeast two-hybrid binding assays. Substitution of Ala for either Leu-423 or Val-429 completely eliminated peptide binding to the SNT-1 PTB domain, while mutation of Val-414, Leu-417, Arg-425 or Val-427 to Ala significantly reduced binding (FIG. 6A). The reduced protein-protein interactions of the individual FGFR1 mutants were not likely due to variations of protein expression in the yeast cells (FIG. 6A). Particularly, expression levels of the Leu-423-Ala and Val-429-Ala mutants were at least as good as that of the wild type. These mutagenesis data agree with (1) the observed intermolecular NOEs (FIG. 1B); (2) the calculated solvent accessible surface area (particularly for the peptide hydrophobic residues); and (3) amino acid conservation of the juxtamembrane region of the FGFR family (FIG. 1B). In addition, these data are also consistent with results of mutational analysis of FGFR1 and SNT-1 interactions [Ong et al., Mol. Cell. Biol. 20:979-989 (2000)]. Collectively, these results demonstrate that the nature of the protein and peptide binding is highly specific and extensive, with multiple types of interactions stabilizing the complex. It is interesting to note that utilization of the hydrophobic side of the β-sandwich opposite to α1 for protein interactions in SNT-1 is atypical and not seen in other PTB domains [Forman-Kay and Pawson, Curr. Opin. Struct. Biol. 9:690-695 (1999)]. Amino acid residues in the corresponding loops, however, have been shown to interact with phospholipids in the PTB domain of Shc and in the structurally homologous PH domains of several signaling molecules [Lemmon et al., Cell 85:621-624 (1996)]. Remarkably, SNT-1 is also capable of interacting with tyrosine-phosphorylated TRKs, which possess no sequence homology to hFGFR1 (see below), illustrating the unique functional diversity of this conserved PTB domain fold.

Figure 6B:
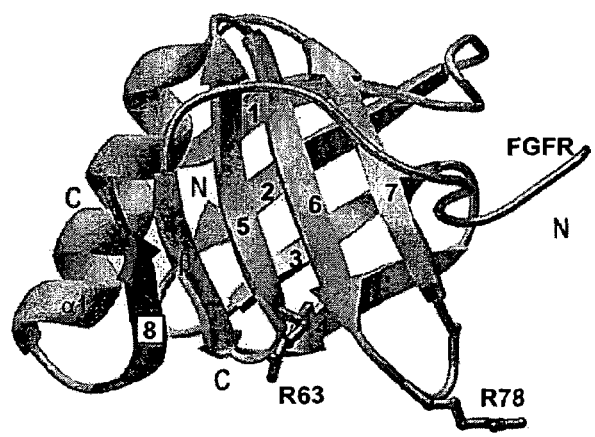
Figure 6C:
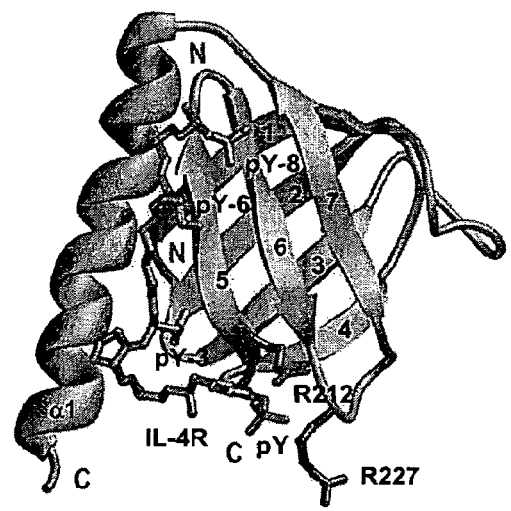
Figure 6D:
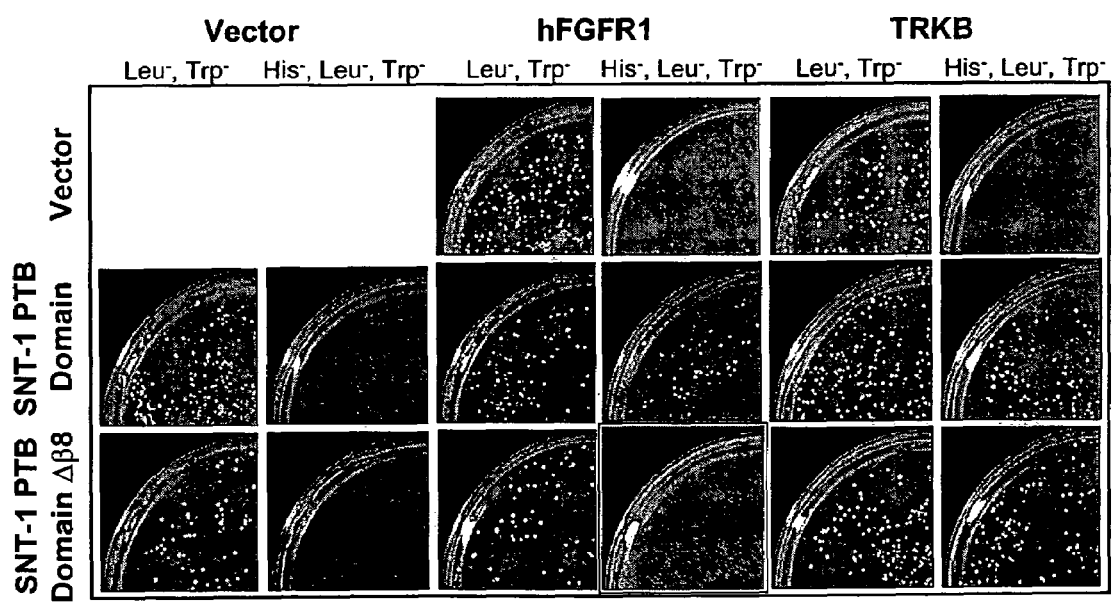

Structural Insights into SNT Binding to Tyrosine-Phosphorylated TRKs: The new SNT-1 PTB domain structure yields insights into how the protein might interact with tyrosine-phosphorylated TRKs. Conserved Arg-63 and Arg-78 residues in SNT-1 are structurally analogous to Arg-212 and Arg-227 of IRS-1 PTB domain, respectively (FIGS. 6B and 6C). The latter pair of Arg residues are essential for IRS-1 binding to phosphotyrosine in the canonical NPXpY motif [Zhou et al., Nat. Struc, Biol. 3:388-393 (1996)]. The mutagenesis and yeast two-hybrid binding studies disclosed herein show that the mutation of Arg-63 and Arg-78 to Gln results in complete elimination of SNT-1 interaction with TRKB, but has no effect on binding to hFGFR1.

Additionally, Ala substitution of Iie (pY-5) in the TRKA peptide (HIIENPQpYFSDA, which is highly homologous to TRKB) caused marked reduction in binding to the PTB domain. Based on these results, the mechanism by which SNT-1 binds to TRKs is appears similar to that of IRS-1 PTB domain interactions with NPXpY-containing proteins (FIG. 6C). Specifically, the phosphotyrosine of the NPXpY motif in TRKs would coordinate with Arg-63 and Arg-78 in SNT-1 PTB domain, and residues N-terminal to the phosphotyrosine would adopt an extended conformation with hydrophobic side-chains intercalating into the hydrophobic pocket between β5 and α1, which is also a site for interactions with hFGFR1. Furthermore, NMR titration experiments showed that hFGFR1 and TRK peptides compete for binding to the PTB domain, which agrees with the results of the peptide competition experiments in a SNT-1 GST pull-down assay [Ong et al., Mol. Cell. Biol. 20:979-989 (2000)]. Together, these results demonstrate that the binding of SNT-1 to either non-phosphorylated FGFRs or tyrosine-phosphorylated TRKs is mutually exclusive.

Regulation of SNT and FGFR Association by a Possible Local Conformational Change: The β8 strand is structurally unique for the PTB domain fold. It was therefore determined whether it was functionally important for SNT-1 binding to hFGFR1 or phosphorylated TRKs. Truncation studies of SNT-1 were therefore performed to address this question. Yeast two-hybrid assays showed that a truncated SNT-1 PTB domain lacking the β8 region (residues 2-111) almost abolished its ability to interact with hFGFR1, without decreasing its TRKB binding (FIG. 6C). Another SNT-1 truncation mutant (residues 11-114), which ends with β8 shortened by one residue, showed markedly reduced binding to hFGFR1 peptide in NMR binding studies (supported by significant line-broadening of the protein NMR signals), but did not impair its interactions with the tyrosine-phosphorylated TRKB peptide. The effects of the β8 truncation were further confirmed in ITC measurements of the SNT PTB domain binding to hFGFR1 or TRK peptides. These results indicate that both the presence and structural integrity of the β8 region are necessary for SNT-1 binding to FGFRs but not for its interaction with TRKs. While the overall structural fold of the SNT-1 PTB domain may be similar in its free, TRK- or hFGFR1-bound forms, the structural requirement of β8 is unique for its hFGFR1 association. This observation is consistent with the fact that the anti-parallel β' strand of the hFGFR1 peptide (7 residues, FIG. 6A) is much longer than these NPXpY or related sequences that are recognized by the PTB domains of Shc [Zhou et al., *J. Biol. Chem.* 270:31119-31123 (1995)], IRS-1 [Zhou et al., *Nature Struct. Biol.* 3:388-393 (1996), Eck et al., *Cell* 85:695-705 (1996)], or Numb [Zwahlen et al., *EMBO J* 19:1505-1515 (2000)]. These findings imply that conformational perturbation of β8 would compromise SNT-1 binding to FGFRs, indicating that this β8 strand could act as an on/off switch for SNT-1/FGFR association.

Possible Role of SNTs as Molecular Switches in FGFR and TRK Signaling: The present structural and mutational analyses of the SNT-1 PTB domain suggest mechanisms by which SNTs coordinate FGF and neurotrophin signaling during neuronal differentiation. The ability of SNTs to interact with non-phosphorylated FGFR raises the possibility that SNTs are sequestered by FGFRs in unstimulated cells and are only available for activation by FGFs. Events that trigger release of SNTs from constitutive FGFR association would allow for SNT interaction with TRKs, leading to a neurotrophin-responsive state in differentiating neurons. Such events may include FGF receptor down-regulation or conformational perturbation to the β8 region of the SNT PTB domain by post-translational modifications or interactions with other protein(s). Alternatively, even in the absence of SNT/FGFR complexes, the conformational flexibility of the SNT PTB domain may be constrained during neurogenesis to regulate its availability for interaction with and activation by neurotrophin receptors. These models may provide new clues to explain how differentiating neuronal precursors undergo the well-documented switch from FGF dependence to neurotrophin dependence [Birren and Anderson *Neuron* 4:189-201 (1990); Ip et al., *Neuron* 13:443-455 (1994); and Stemple et al., *Neuron* 1:517-525 (1988)], which is not simply due to changes in TRK expression [Ip et al., *Neuron* 13:443-455 (1994)].

Conclusion

The new three-dimensional structure of the SNT-1 PTB domain/hFGFR1 complex reveals the unique features that enable SNT-1 to recognize two radically different receptor sequences in a mutually exclusive manner. The results demonstrate that both adaptive hydrophobic interactions as well as complementary electrostatic interactions are important factors that underlie specificity and versatility of molecular recognition by the conserved PTB domain structural fold. These findings further indicate that cellular events, which cause a local conformational change in the PTB domain, may govern SNT interactions with either FGFRs or TRKs. Thus, the intrinsic adaptability and flexibility of the SNT PTB domain appears to serve as a focal point for the essential interplay between FGF and neurotrophin receptor signaling that governs neuronal survival and differentiation.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are hereby incorporated by reference herein in their entireties.

What is claimed is:

1. An isolated peptide derived from FGFR1 consisting of 16 to 50 amino acids comprising the amino acid sequence of SEQ ID NO:5: Val Xaa Xaa Leu Xaa Xaa Xaa Ile Xaa Leu Xaa Arg Xaa Val Xaa Val.

2. An isolated peptide derived from FGFR1 consisting of 16 to 50 amino acids comprising the amino acid sequence of SEQ ID NO:3.

* * * * *

UNITED STATES PATENT AND TRADEMARK OFFICE
CERTIFICATE OF CORRECTION

PATENT NO. : 7,645,857 B2
APPLICATION NO. : 11/183567
DATED : January 12, 2010
INVENTOR(S) : Ming-Ming Zhou and Mitchell Goldfarb It is certified that error appears in the above-identified patent and that said Letters Patent is hereby corrected as shown below:

Col. 1, line 16 the statement of Governmental Support should read as follows:

This invention was made with government support under GM059432 awarded by the National Institutes of Health. The government has certain rights in this invention.

Signed and Sealed this

Twentieth Day of July, 2010

David J. Kappos
*Director of the United States Patent and Trademark Office*

SEQUENCE LISTING

```
<160> NUMBER OF SEQ ID NOS: 33

<210> SEQ ID NO 1
<211> LENGTH: 508
<212> TYPE: PRT
<213> ORGANISM: Homo sapiens

<400> SEQUENCE: 1

Met Gly Ser Cys Cys Ser Cys Pro Asp Lys Asp Thr Val Pro Asp Asn
1               5                   10                  15

His Arg Asn Lys Phe Lys Val Ile Asn Val Asp Asp Asp Gly Asn Glu
            20                  25                  30

Leu Gly Ser Gly Ile Met Glu Leu Thr Asp Thr Glu Leu Ile Leu Tyr
        35                  40                  45

Thr Arg Lys Arg Asp Ser Val Lys Trp His Tyr Leu Cys Leu Arg Arg
    50                  55                  60

Tyr Gly Tyr Asp Ser Asn Leu Phe Ser Phe Glu Ser Gly Arg Arg Cys
65                  70                  75                  80

Gln Thr Gly Gln Gly Ile Phe Ala Phe Lys Cys Ala Arg Ala Glu Glu
                85                  90                  95

Leu Phe Asn Met Leu Gln Glu Ile Met Gln Asn Asn Ser Ile Asn Val
            100                 105                 110

Val Glu Glu Pro Val Val Glu Arg Asn Asn His Gln Thr Glu Leu Glu
        115                 120                 125
```

Val Pro Arg Thr Pro Arg Thr Pro Thr Thr Pro Gly Phe Ala Ala Gln
    130                 135                 140

Asn Leu Pro Asn Gly Tyr Pro Arg Tyr Pro Ser Phe Gly Asp Ala Ser
145                 150                 155                 160

Ser His Pro Ser Ser Arg His Pro Ser Val Gly Ser Ala Arg Leu Pro
                165                 170                 175

Ser Val Gly Glu Glu Ser Thr His Pro Leu Leu Val Ala Glu Glu Gln
            180                 185                 190

Val His Thr Tyr Val Asn Thr Thr Gly Val Gln Glu Glu Arg Lys Asn
            195                 200                 205

Arg Thr Ser Val His Val Pro Leu Glu Ala Arg Val Ser Asn Ala Glu
        210                 215                 220

Ser Ser Thr Pro Lys Glu Glu Pro Ser Ser Ile Glu Asp Arg Asp Pro
225                 230                 235                 240

Gln Ile Leu Leu Glu Pro Glu Gly Val Lys Phe Val Leu Gly Pro Thr
                245                 250                 255

Pro Val Gln Lys Gln Leu Met Glu Lys Glu Lys Leu Glu Gln Leu Gly
            260                 265                 270

Arg Asp Gln Val Ser Gly Ser Gly Ala Asn Asn Thr Glu Trp Asp Thr
        275                 280                 285

Gly Tyr Asp Ser Asp Glu Arg Arg Asp Ala Pro Ser Val Asn Lys Leu
    290                 295                 300

Val Tyr Glu Asn Ile Asn Gly Leu Ser Ile Pro Ser Ala Ser Gly Val
305                 310                 315                 320

Arg Arg Gly Arg Leu Thr Ser Thr Ser Thr Ser Asp Thr Gln Asn Ile
                325                 330                 335

Asn Asn Ser Ala Gln Arg Arg Thr Ala Leu Leu Asn Tyr Glu Asn Leu
            340                 345                 350

Pro Ser Leu Pro Pro Val Trp Glu Ala Arg Lys Leu Ser Arg Asp Glu
        355                 360                 365

Asp Asp Asn Leu Gly Pro Lys Thr Pro Ser Leu Asn Gly Tyr His Asn
    370                 375                 380

Asn Leu Asp Pro Met His Asn Tyr Val Asn Thr Glu Asn Val Thr Val
385                 390                 395                 400

Pro Ala Ser Ala His Lys Ile Glu Tyr Ser Arg Arg Arg Asp Cys Thr
                405                 410                 415

Pro Thr Val Phe Asn Phe Asp Ile Arg Arg Pro Ser Leu Glu His Arg
            420                 425                 430

Gln Leu Asn Tyr Ile Gln Val Asp Leu Glu Gly Gly Ser Asp Ser Asp
        435                 440                 445

Asn Pro Gln Thr Pro Lys Thr Pro Thr Thr Pro Leu Pro Gln Thr Pro
    450                 455                 460

Thr Arg Arg Thr Glu Leu Tyr Ala Val Ile Asp Ile Glu Arg Thr Ala
465                 470                 475                 480

Ala Met Ser Asn Leu Gln Lys Ala Leu Pro Arg Asp Asp Gly Thr Ser
                485                 490                 495

Arg Lys Thr Arg His Asn Ser Thr Asp Leu Pro Met
            500                 505

<210> SEQ ID NO 2
<211> LENGTH: 822
<212> TYPE: PRT
<213> ORGANISM: Mus musculus

<400> SEQUENCE: 2

```
Met Trp Gly Trp Lys Cys Leu Leu Phe Trp Ala Val Leu Val Thr Ala
 1               5                  10                  15

Thr Leu Cys Thr Ala Arg Pro Ala Pro Thr Leu Pro Glu Gln Ala Gln
             20                  25                  30

Pro Trp Gly Val Pro Val Glu Val Glu Ser Leu Leu Val His Pro Gly
         35                  40                  45

Asp Leu Leu Gln Leu Arg Cys Arg Leu Arg Asp Asp Val Gln Ser Ile
     50                  55                  60

Asn Trp Leu Arg Asp Gly Val Gln Leu Val Glu Ser Asn Arg Thr Arg
65                  70                  75                  80

Ile Thr Gly Glu Glu Val Glu Val Arg Asp Ser Ile Pro Ala Asp Ser
                 85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Arg Arg Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175

Lys Cys Pro Ser Ser Gly Thr Pro Asn Pro Thr Leu Arg Trp Leu Lys
            180                 185                 190

Asn Gly Lys Glu Phe Lys Pro Asp His Arg Ile Gly Gly Tyr Lys Val
        195                 200                 205

Arg Tyr Ala Thr Trp Ser Ile Ile Met Asp Ser Val Val Pro Ser Asp
    210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
                245                 250                 255

Leu Gln Ala Gly Leu Pro Ala Asn Glu Thr Val Ala Leu Gly Ser Asn
            260                 265                 270

Val Glu Phe Met Cys Lys Val Tyr Ser Asp Pro Gln Pro His Ile Gln
        275                 280                 285

Trp Leu Lys His Ile Glu Val Asn Gly Ser Lys Ile Gly Pro Asp Asn
    290                 295                 300

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
                325                 330                 335

Gly Glu Tyr Thr Cys Leu Ala Gly Asn Ser Ile Gly Leu Ser His His
            340                 345                 350

Ser Ala Trp Leu Thr Val Leu Glu Ala Leu Glu Glu Arg Pro Ala Val
        355                 360                 365

Met Thr Ser Pro Leu Tyr Leu Glu Ile Ile Ile Tyr Cys Thr Gly Ala
    370                 375                 380

Phe Leu Ile Ser Cys Met Leu Gly Ser Val Ile Ile Tyr Lys Met Lys
385                 390                 395                 400

Ser Gly Thr Lys Lys Ser Asp Phe His Ser Gln Met Ala Val His Lys
                405                 410                 415
```

```
Leu Ala Lys Ser Ile Pro Leu Arg Arg Gln Val Thr Val Ser Ala Asp
            420                 425                 430

Ser Ser Ala Ser Met Asn Ser Gly Val Leu Leu Val Arg Pro Ser Arg
            435                 440                 445

Leu Ser Ser Ser Gly Thr Pro Met Pro Ala Gly Val Ser Glu Tyr Glu
            450                 455                 460

Leu Pro Glu Asp Pro Arg Trp Glu Leu Pro Arg Asp Arg Leu Val Leu
465                 470                 475                 480

Gly Lys Pro Leu Gly Glu Gly Cys Phe Gly Gln Val Val Leu Ala Glu
            485                 490                 495

Ala Ile Gly Leu Asp Lys Asp Lys Pro Asn Arg Val Thr Lys Val Ala
            500                 505                 510

Val Lys Met Leu Lys Ser Asp Ala Thr Glu Lys Asp Leu Ser Asp Leu
            515                 520                 525

Ile Ser Glu Met Glu Met Met Lys Met Ile Gly Lys His Lys Asn Ile
            530                 535                 540

Ile Asn Leu Leu Gly Ala Cys Thr Gln Asp Gly Pro Leu Tyr Val Ile
545                 550                 555                 560

Val Glu Tyr Ala Ser Lys Gly Asn Leu Arg Glu Tyr Leu Gln Ala Arg
            565                 570                 575

Arg Pro Pro Gly Leu Glu Tyr Cys Tyr Asn Pro Ser His Asn Pro Glu
            580                 585                 590

Glu Gln Leu Ser Ser Lys Asp Leu Val Ser Cys Ala Tyr Gln Val Ala
            595                 600                 605

Arg Gly Met Glu Tyr Leu Ala Ser Lys Lys Cys Ile His Arg Asp Leu
            610                 615                 620

Ala Ala Arg Asn Val Leu Val Thr Glu Asp Asn Val Met Lys Ile Ala
625                 630                 635                 640

Asp Phe Gly Leu Ala Arg Asp Ile His His Ile Asp Tyr Tyr Lys Lys
            645                 650                 655

Thr Thr Asn Gly Arg Leu Pro Val Lys Trp Met Ala Pro Glu Ala Leu
            660                 665                 670

Phe Asp Arg Ile Tyr Thr His Gln Ser Asp Val Trp Ser Phe Gly Val
            675                 680                 685

Leu Leu Trp Glu Ile Phe Thr Leu Gly Gly Ser Pro Tyr Pro Gly Val
            690                 695                 700

Pro Val Glu Glu Leu Phe Lys Leu Leu Lys Glu Gly His Arg Met Asp
705                 710                 715                 720

Lys Pro Ser Asn Cys Thr Asn Glu Leu Tyr Met Met Met Arg Asp Cys
            725                 730                 735

Trp His Ala Val Pro Ser Gln Arg Pro Thr Phe Lys Gln Leu Val Glu
            740                 745                 750

Asp Leu Asp Arg Ile Val Ala Leu Thr Ser Ser Gln Glu Tyr Leu Asp
            755                 760                 765

Leu Ser Ile Pro Leu Asp Gln Tyr Ser Pro Ser Phe Pro Asp Thr Arg
            770                 775                 780

Ser Ser Thr Cys Ser Ser Gly Glu Asp Ser Val Phe Ser His Glu Pro
785                 790                 795                 800

Leu Pro Glu Glu Pro Cys Leu Pro Arg His Pro Thr Gln Leu Ala Asn
            805                 810                 815

Ser Gly Leu Lys Arg Arg
            820
```

```
<210> SEQ ID NO 3
<211> LENGTH: 22
<212> TYPE: PRT
<213> ORGANISM: Mus musculus

<400> SEQUENCE: 3

His Ser Gln Met Ala Val His Lys Leu Ala Lys Ser Ile Pro Leu Arg
 1               5                  10                  15

Arg Gln Val Thr Val Ser
            20

<210> SEQ ID NO 4
<211> LENGTH: 11
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (9)...(9)
<223> OTHER INFORMATION: Xaa is a phosphotyrosine

<400> SEQUENCE: 4

Leu Val Ile Ala Gly Asn Pro Ala Xaa Arg Ser
 1               5                  10

<210> SEQ ID NO 5
<211> LENGTH: 16
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (2)...(3)
<223> OTHER INFORMATION: Xaa = Any Amino Acid
<220> FEATURE:
<221> NAME/KEY: misc_feature
<222> LOCATION: (5)...(7)
<223> OTHER INFORMATION: Xaa = Any Amino Acid
<220> FEATURE:
<221> NAME/KEY: misc_feature
<222> LOCATION: (9)...(9)
<223> OTHER INFORMATION: Xaa = Any Amino Acid
<220> FEATURE:
<221> NAME/KEY: misc_feature
<222> LOCATION: (11)...(11)
<223> OTHER INFORMATION: Xaa = Any Amino Acid
<220> FEATURE:
<221> NAME/KEY: misc_feature
<222> LOCATION: (13)...(13)
<223> OTHER INFORMATION: Xaa = Any Amino Acid
<220> FEATURE:
<221> NAME/KEY: misc_feature
<222> LOCATION: (15)...(15)
<223> OTHER INFORMATION: Xaa = Any Amino Acid

<400> SEQUENCE: 5

Val Xaa Xaa Leu Xaa Xaa Xaa Ile Xaa Leu Xaa Arg Xaa Val Xaa Val
 1               5                  10                  15

<210> SEQ ID NO 6
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (3)...(3)
<223> OTHER INFORMATION: Xaa = Any Amino Acid
```

```
<220> FEATURE:
<221> NAME/KEY: misc_feature
<222> LOCATION: (4)...(4)
<223> OTHER INFORMATION: Xaa is a phosphotyrosine

<400> SEQUENCE: 6

Asn Pro Xaa Xaa
  1

<210> SEQ ID NO 7
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (8)...(8)
<223> OTHER INFORMATION: Xaa is a phosphotyrosine

<400> SEQUENCE: 7

His Ile Ile Glu Asn Pro Gln Xaa Phe Ser Asp Ala
  1               5                  10

<210> SEQ ID NO 8
<211> LENGTH: 55
<212> TYPE: PRT
<213> ORGANISM: Homo sapiens

<400> SEQUENCE: 8

Asp Asn His Arg Asn Lys Phe Lys Val Ile Asn Val Asp Asp Asp Gly
  1               5                  10                  15

Asn Glu Leu Gly Ser Gly Ile Met Glu Leu Thr Asp Thr Glu Leu Ile
             20                  25                  30

Leu Tyr Thr Arg Lys Arg Asp Ser Val Lys Trp His Tyr Leu Cys Leu
         35                  40                  45

Arg Arg Tyr Gly Tyr Asp Ser
     50                  55

<210> SEQ ID NO 9
<211> LENGTH: 55
<212> TYPE: PRT
<213> ORGANISM: Homo sapiens

<400> SEQUENCE: 9

Asp Asn His Pro Thr Lys Phe Lys Val Thr Asn Val Asp Asp Glu Gly
  1               5                  10                  15

Val Glu Leu Gly Ser Gly Val Met Glu Leu Thr Gln Ser Glu Leu Val
             20                  25                  30

Leu His Leu His Arg Arg Glu Ala Val Arg Trp Pro Tyr Leu Cys Leu
         35                  40                  45

Arg Arg Tyr Gly Tyr Asp Ser
     50                  55

<210> SEQ ID NO 10
<211> LENGTH: 61
<212> TYPE: PRT
<213> ORGANISM: Homo sapiens

<400> SEQUENCE: 10

Pro Ala Phe Lys Glu Val Trp Gln Val Ile Leu Lys Pro Lys Gly Leu
  1               5                  10                  15

Gly Gln Thr Lys Asn Leu Ile Gly Ile Tyr Arg Leu Cys Leu Thr Ser
```

```
                20                  25                  30
Lys Thr Ile Ser Phe Val Lys Leu Asn Ser Glu Ala Ala Val Val
         35                  40                  45

Leu Gln Leu Met Asn Ile Arg Arg Cys Gly His Ser Glu
 50                  55                  60

<210> SEQ ID NO 11
<211> LENGTH: 61
<212> TYPE: PRT
<213> ORGANISM: Homo sapiens

<400> SEQUENCE: 11

Ala Ala Tyr Arg Glu Val Trp Gln Val Asn Leu Lys Pro Lys Gly Leu
 1               5                  10                  15

Gly Gln Ser Lys Asn Leu Thr Gly Val Tyr Arg Leu Cys Leu Ser Ala
             20                  25                  30

Arg Thr Ile Gly Phe Val Lys Leu Asn Cys Glu Gln Pro Ser Val Thr
         35                  40                  45

Leu Gln Leu Met Asn Ile Arg Arg Cys Gly His Ser Asp
 50                  55                  60

<210> SEQ ID NO 12
<211> LENGTH: 61
<212> TYPE: PRT
<213> ORGANISM: Mus musculus

<400> SEQUENCE: 12

Ala Val Tyr Arg Glu Val Trp Gln Val Asn Leu Lys Pro Lys Gly Leu
 1               5                  10                  15

Gly Gln Ser Lys Asn Leu Thr Gly Val Tyr Arg Leu Cys Leu Ser Ala
             20                  25                  30

Arg Thr Ile Gly Phe Val Lys Leu Asn Cys Glu Gly Pro Ser Val Thr
         35                  40                  45

Leu Gln Leu Asn Asn Ile Arg Arg Cys Gly His Ser Asp
 50                  55                  60

<210> SEQ ID NO 13
<211> LENGTH: 61
<212> TYPE: PRT
<213> ORGANISM: Homo sapiens

<400> SEQUENCE: 13

Pro Phe Tyr Lys Asp Val Trp Gln Val Ile Val Lys Pro Arg Gly Leu
 1               5                  10                  15

Gly His Arg Lys Glu Leu Ser Gly Val Phe Arg Leu Cys Leu Thr Asp
             20                  25                  30

Glu Glu Val Val Phe Val Arg Leu Asn Thr Glu Val Ala Ser Val Val
         35                  40                  45

Val Gln Leu Leu Ser Ile Arg Arg Cys Gly His Ser Glu
 50                  55                  60

<210> SEQ ID NO 14
<211> LENGTH: 61
<212> TYPE: PRT
<213> ORGANISM: Mus musculus

<400> SEQUENCE: 14

Pro Phe Tyr Lys Asp Val Trp Gln Val Val Val Lys Pro Arg Gly Leu
 1               5                  10                  15
```

```
Gly His Arg Lys Glu Leu Ser Gly Val Phe Arg Leu Cys Leu Thr Asp
             20                  25                  30

Glu Glu Val Val Phe Val Arg Leu Asn Thr Glu Val Ala Ser Val Val
             35                  40                  45

Val Gln Leu Leu Ser Ile Arg Arg Cys Gly His Ser Glu
 50                  55                  60
```

<210> SEQ ID NO 15
<211> LENGTH: 72
<212> TYPE: PRT
<213> ORGANISM: Mus musculus

<400> SEQUENCE: 15

```
Ala Pro Phe Gln Asp Val Trp Pro Val Thr Leu Arg Ser Lys Gly Leu
 1               5                  10                  15

Gly Arg Ala Gln Gly Leu Ser Ser Gly Ser Tyr Arg Leu Cys Leu Gly
             20                  25                  30

Ser Gly Ala Leu Ser Leu Leu Arg Lys Pro Gly Ser Lys Gly Ser Arg
             35                  40                  45

Asp Ser Arg Ala Thr Pro Pro Pro Val Leu Arg Leu Ser Leu Leu Ser
 50                  55                  60

Val Arg Arg Cys Gly His Ala Asp
 65                  70
```

<210> SEQ ID NO 16
<211> LENGTH: 71
<212> TYPE: PRT
<213> ORGANISM: Homo sapiens

<400> SEQUENCE: 16

```
Asn Leu Phe Ser Phe Glu Ser Gly Arg Arg Cys Gln Thr Gly Gln Gly
 1               5                  10                  15

Ile Phe Ala Phe Lys Cys Ala Arg Ala Glu Glu Leu Phe Asn Met Leu
             20                  25                  30

Gln Glu Ile Met Gln Asn Asn Ser Ile Asn Val Val Glu Glu Pro Val
             35                  40                  45

Val Glu Arg Asn Asn His Gln Thr Glu Leu Glu Val Pro Arg Thr Pro
 50                  55                  60

Arg Thr Pro Thr Thr Pro Gly
 65                  70
```

<210> SEQ ID NO 17
<211> LENGTH: 72
<212> TYPE: PRT
<213> ORGANISM: Homo sapiens

<400> SEQUENCE: 17

```
Asn Leu Phe Ser Phe Glu Ser Gly Arg Arg Cys Gln Thr Gly Gln Gly
 1               5                  10                  15

Ile Phe Ala Phe Lys Cys Ser Arg Ala Glu Glu Ile Phe Asn Leu Leu
             20                  25                  30

Gln Asp Leu Met Gln Cys Asn Ser Ile Asn Val Met Glu Pro Val
             35                  40                  45

Ile Ile Thr Arg Asn Ser His Pro Ala Glu Leu Asp Leu Pro Arg Ala
 50                  55                  60

Pro Gln Pro Pro Asn Ala Leu Gly
 65                  70
```

```
<210> SEQ ID NO 18
<211> LENGTH: 49
<212> TYPE: PRT
<213> ORGANISM: Homo sapiens

<400> SEQUENCE: 18

Asn Phe Phe Phe Ile Glu Val Gly Arg Ser Ala Val Thr Gly Pro Gly
 1               5                  10                  15

Glu Phe Trp Met Gln Val Asp Asp Ser Val Val Ala Gln Asn Met His
            20                  25                  30

Glu Thr Ile Leu Glu Ala Met Arg Ala Met Ser Asp Glu Phe Arg Pro
        35                  40                  45

Arg

<210> SEQ ID NO 19
<211> LENGTH: 49
<212> TYPE: PRT
<213> ORGANISM: Homo sapiens

<400> SEQUENCE: 19

Ser Phe Phe Phe Ile Glu Val Gly Arg Ser Ala Val Thr Gly Pro Gly
 1               5                  10                  15

Glu Leu Trp Met Gln Ala Asp Asp Ser Val Val Ala Gln Asn Ile His
            20                  25                  30

Glu Thr Ile Leu Glu Ala Met Lys Ala Leu Lys Glu Leu Phe Glu Phe
        35                  40                  45

Arg

<210> SEQ ID NO 20
<211> LENGTH: 49
<212> TYPE: PRT
<213> ORGANISM: Mus musculus

<400> SEQUENCE: 20

Ser Phe Phe Phe Ile Glu Val Gly Arg Ser Ala Val Thr Gly Pro Gly
 1               5                  10                  15

Glu Leu Trp Met Gln Val Asp Asp Ser Val Val Ala Gln Asn Ile His
            20                  25                  30

Glu Thr Ile Leu Glu Ala Met Lys Ala Leu Lys Glu Leu Phe Glu Phe
        35                  40                  45

Arg

<210> SEQ ID NO 21
<211> LENGTH: 49
<212> TYPE: PRT
<213> ORGANISM: Homo sapiens

<400> SEQUENCE: 21

Gln Tyr Phe Phe Leu Glu Val Gly Arg Ser Thr Val Ile Gly Pro Gly
 1               5                  10                  15

Glu Leu Trp Met Gln Val Asp Asp Cys Val Val Ala Gln Asn Met His
            20                  25                  30

Glu Leu Phe Leu Glu Lys Met Arg Ala Leu Cys Ala Asp Glu Tyr Arg
        35                  40                  45

Ala

<210> SEQ ID NO 22
<211> LENGTH: 49
<212> TYPE: PRT
```

<213> ORGANISM: Mus musculus

<400> SEQUENCE: 22

Gln Tyr Phe Phe Leu Glu Val Gly Arg Ser Thr Val Ile Gly Pro Gly
1               5                   10                  15

Glu Leu Trp Met Gln Val Asp Asp Ser Val Val Ala Gln Asn Met His
            20                  25                  30

Glu Leu Phe Leu Glu Lys Met Arg Ala Leu Cys Ala Asp Glu Tyr Arg
        35                  40                  45

Ala

<210> SEQ ID NO 23
<211> LENGTH: 49
<212> TYPE: PRT
<213> ORGANISM: Mus musculus

<400> SEQUENCE: 23

Ser Phe Phe Phe Leu Glu Leu Gly Arg Ser Ala Pro Ile Gly Pro Gly
1               5                   10                  15

Glu Leu Trp Leu Gln Ala Pro Asp Ala Val Ala Gln Ser Ile His
            20                  25                  30

Glu Thr Val Leu Ala Ala Met Lys Arg Leu Gly Ser Asn Ala Ala Gly
        35                  40                  45

Lys

<210> SEQ ID NO 24
<211> LENGTH: 22
<212> TYPE: PRT
<213> ORGANISM: Homo sapiens

<400> SEQUENCE: 24

His Ser Gln Met Ala Val His Lys Leu Ala Lys Ser Ile Pro Leu Arg
1               5                   10                  15

Arg Gln Val Thr Val Ser
            20

<210> SEQ ID NO 25
<211> LENGTH: 22
<212> TYPE: PRT
<213> ORGANISM: Xenopus laevis

<400> SEQUENCE: 25

Asn Ser Gln Leu Ala Val His Lys Leu Ala Lys Ser Ile Pro Val Arg
1               5                   10                  15

Arg Gln Val Thr Val Ser
            20

<210> SEQ ID NO 26
<211> LENGTH: 22
<212> TYPE: PRT
<213> ORGANISM: Homo sapiens

<400> SEQUENCE: 26

Ser Ser Gln Pro Ala Val His Lys Leu Thr Lys Arg Ile Pro Leu Arg
1               5                   10                  15

Arg Gln Val Thr Val Ser
            20

<210> SEQ ID NO 27
<211> LENGTH: 22

```
<212> TYPE: PRT
<213> ORGANISM: Xenopus laevis

<400> SEQUENCE: 27

Phe Thr Gly Pro Pro Val His Lys Leu Thr Lys Arg Ile Pro Leu His
 1               5                  10                  15

Arg Gln Val Thr Val Ser
            20

<210> SEQ ID NO 28
<211> LENGTH: 20
<212> TYPE: PRT
<213> ORGANISM: Homo sapiens

<400> SEQUENCE: 28

Gly Ser Pro Thr Val His Lys Ile Ser Arg Phe Pro Leu Lys Arg Gln
 1               5                  10                  15

Val Ser Leu Glu
            20

<210> SEQ ID NO 29
<211> LENGTH: 20
<212> TYPE: PRT
<213> ORGANISM: Mus musculus

<400> SEQUENCE: 29

Gly Ser Pro Thr Val His Lys Val Ser Arg Phe Pro Leu Lys Arg Gln
 1               5                  10                  15

Val Ser Leu Glu
            20

<210> SEQ ID NO 30
<211> LENGTH: 21
<212> TYPE: PRT
<213> ORGANISM: Xenopus laevis

<400> SEQUENCE: 30

Thr Ala Pro Pro Val His Lys Val Ser Arg Phe Pro Leu Lys Arg Gln
 1               5                  10                  15

Gln Val Ser Leu Glu
            20

<210> SEQ ID NO 31
<211> LENGTH: 21
<212> TYPE: PRT
<213> ORGANISM: Homo sapiens

<400> SEQUENCE: 31

Arg Pro Pro Ala Thr Val Gln Lys Leu Ser Arg Phe Pro Leu Ala Arg
 1               5                  10                  15

Gln Phe Ser Leu Glu
            20

<210> SEQ ID NO 32
<211> LENGTH: 21
<212> TYPE: PRT
<213> ORGANISM: Mus musculus

<400> SEQUENCE: 32

Arg Gln Pro Val Thr Ile Gln Lys Leu Ser Arg Phe Pro Leu Ala Arg
 1               5                  10                  15

Gln Phe Ser Leu Glu
```

```
<210> SEQ ID NO 33
<211> LENGTH: 21
<212> TYPE: PRT
<213> ORGANISM: Xenopus laevis

<400> SEQUENCE: 33

Leu Gln Thr Pro Thr Val His Lys Leu Ala Lys Phe Pro Leu Ile Arg
 1               5                  10                  15

Gln Phe Ser Leu Glu
            20
```